US012599478B2

(12) United States Patent
Oh

(10) Patent No.: US 12,599,478 B2
(45) Date of Patent: Apr. 14, 2026

(54) LIFTING SUTURE FOR RHINOPLASTY AND MANUFACTURING METHOD THEREOF

(71) Applicants:DONGBANG MEDICAL CO., LTD., Chungcheongnam-do (KR); Hae seok Oh, Seoul (KR)

(72) Inventor: Hae seok Oh, Seoul (KR)

(73) Assignees: DONGBANG MEDICAL CO., LTD., Chungcheongnam-do (KR); Hae seok Oh, Seoul (KR)

( * ) Notice: Subject to any disclaimer, the term of this patent is extended or adjusted under 35 U.S.C. 154(b) by 0 days.

(21) Appl. No.: 18/382,060

(22) Filed: Oct. 20, 2023

(65) Prior Publication Data

US 2024/0041591 A1     Feb. 8, 2024

Related U.S. Application Data

(63) Continuation of application No. PCT/KR2022/001039, filed on Jan. 20, 2022.

(30) Foreign Application Priority Data

Nov. 9, 2021     (KR) ........................ 10-2021-0153302
Nov. 9, 2021     (KR) ........................ 10-2021-0153309
(Continued)

(51) Int. Cl.
A61B 17/06          (2006.01)
A61F 2/18           (2006.01)
A61B 17/00          (2006.01)

(52) U.S. Cl.
CPC ........ A61F 2/186 (2013.01); A61B 17/06166 (2013.01); A61B 2017/00526 (2013.01)

(58) Field of Classification Search
CPC ...................... A61F 2/186; A61B 2017/06166
See application file for complete search history.

(56) References Cited

U.S. PATENT DOCUMENTS 2,093,145  A  *   9/1937   Carruthers .............. A61L 17/08
                                                        8/94.11
4,643,178  A  *   2/1987   Nastari .............. A61B 17/8861
                                                        606/103
(Continued)

FOREIGN PATENT DOCUMENTS

KR     10-2013-0020123  A     2/2013
KR     10-2016-0130906  A     11/2016
(Continued)

OTHER PUBLICATIONS

WIPO, International Search Report and International Written Opinion for International Application No. PCT/KR2022/001039, 2022. 05.11, 9 pages.
(Continued)

*Primary Examiner* — Alexander J Orkin
(74) *Attorney, Agent, or Firm* — Nicholas Park

(57)          ABSTRACT

Disclosed are a lifting suture for rhinoplasty and a manufacturing method thereof. A manufacturing method of a lifting suture according to one embodiment of the present disclosure may include forming a lifting suture including a first region and a second region, each of which has cogs formed therein, and forming a connecting region by pressing the lifting suture while the first region and the second region are bent so that a first angle is formed therebetween.

5 Claims, 39 Drawing Sheets

(30)          Foreign Application Priority Data

| | | |
|---|---|---|
| Nov. 9, 2021 | (KR) ........................ | 10-2021-0153311 |
| Dec. 2, 2021 | (KR) ........................ | 10-2021-0170928 |
| Jan. 12, 2022 | (KR) ........................ | 10-2022-0004805 |

(56)                References Cited

U.S. PATENT DOCUMENTS

| | | | | |
|---|---|---|---|---|
| 5,500,000 | A * | 3/1996 | Feagin ............... | A61B 17/0401 606/220 |
| 5,645,568 | A * | 7/1997 | Chervitz .......... | A61B 17/06166 606/228 |
| 2002/0173848 | A1 * | 11/2002 | Sachs ................... | A61F 2/0059 606/228 |
| 2002/0198544 | A1 * | 12/2002 | Uflacker ............... | A61F 2/0059 606/144 |
| 2005/0267531 | A1 * | 12/2005 | Ruff ..................... | A61B 17/064 606/228 |
| 2007/0239207 | A1 * | 10/2007 | Beramendi ...... | A61B 17/06166 606/228 |
| 2008/0077240 | A1 * | 3/2008 | Saidi ........................ | A61F 2/18 623/10 |
| 2009/0248071 | A1 * | 10/2009 | Saint ............... | A61B 17/06066 606/232 |
| 2009/0299407 | A1 * | 12/2009 | Yuan ............... | A61B 17/06166 606/228 |
| 2010/0137679 | A1 * | 6/2010 | Lashinski .......... | A61B 17/0401 600/37 |
| 2010/0234947 | A1 * | 9/2010 | Ben Rubi .......... | A61B 17/0401 623/11.11 |
| 2010/0241141 | A1 * | 9/2010 | Lee .................. | A61B 17/06166 606/228 |
| 2011/0251634 | A1 * | 10/2011 | Gonzales ........... | A61B 17/0642 606/199 |
| 2011/0319932 | A1 * | 12/2011 | Avelar .................. | A61B 90/90 606/228 |
| 2013/0150872 | A1 * | 6/2013 | Rousseau ............... | A61B 17/06 606/151 |
| 2013/0226233 | A1 * | 8/2013 | D'Agostino ..... | A61B 17/06138 606/228 |
| 2014/0081320 | A1 * | 3/2014 | Sengun .............. | A61B 17/0485 606/223 |
| 2014/0288594 | A1 * | 9/2014 | Shaefers .......... | A61B 17/06166 606/228 |
| 2015/0032154 | A1 * | 1/2015 | Kaplan .............. | A61B 17/0487 606/228 |
| 2015/0066081 | A1 * | 3/2015 | Martin .................... | D04B 1/22 606/228 |
| 2017/0056036 | A1 * | 3/2017 | Jenkins .............. | A61B 17/0401 |
| 2018/0317911 | A1 * | 11/2018 | Jang ......................... | D02J 3/02 |
| 2018/0317912 | A1 * | 11/2018 | Brandi ............. | A61B 17/06166 |

FOREIGN PATENT DOCUMENTS

| | | | |
|---|---|---|---|
| KR | 10-1679813 | B1 | 11/2016 |
| KR | 10-1695339 | B1 | 1/2017 |
| KR | 10-2017-0076089 | A | 7/2017 |
| KR | 10-2018-0034029 | A | 4/2018 |
| KR | 10-2018-0120621 | A | 11/2018 |
| KR | 10-2018-0133111 | A | 12/2018 |
| KR | 10-2019-0080574 | A | 7/2019 |
| KR | 10-2070547 | B1 | 1/2020 |
| KR | 10-2020-0025785 | A | 3/2020 |
| KR | 10-2020-0043134 | A | 4/2020 |
| KR | 20-2020-0001836 | U | 8/2020 |
| KR | 10-2165798 | B1 | 10/2020 |
| KR | 10-2021-0033932 | A | 3/2021 |

OTHER PUBLICATIONS

KIPO, Office Action, Korean Patent Application No. 10-2021-0153302, Jan. 11, 2022.
KIPO, Decision to Grant a Patent, Korean Patent Application No. 10-2021-0153302, Apr. 12, 2022.
China National Intellectual Property Administration, Office Action Issuer for China Patent Application No. CN202280030461.6, Mar. 27, 2024.

* cited by examiner

S10

S11

FORMING A LIFTING SUTURE INCLUDING
FIRST REGION AND SECOND REGION

S12

PRESS LIFTING SUTURE WHILE FIRST REGION
AND SECOND REGION ARE BENT SO THAT
PREDETERMINED ANGLE IS FORMED THEREBETWEEN

LIFTING SUTURE FOR RHINOPLASTY AND MANUFACTURING METHOD THEREOF

CROSS-REFERENCE TO RELATED APPLICATION

This application is a US Bypass Continuation Application of International Application No. PCT/KR2022/001039, filed on Jan. 20, 2022, which claims priority to and the benefit of Korean Patent Application No. 10-2021-0153302, filed on Nov. 9, 2021, Korean Patent Application No. 10-2021-0153309, filed on Nov. 9, 2021, Korean Patent Application No. 10-2021-0153311, filed on Nov. 9, 2021, Korean Patent Application No. 10-2021-0170928, filed on Dec. 2, 2021, and Korean Patent Application No. 10-2022-0004805, filed on Jan. 12, 2022, the disclosure of which is incorporated herein by reference in its entirety.

BACKGROUND

Technical Field

The present disclosure relates to a lifting suture, and more particularly, to a lifting suture utilized in rhinoplasty.

Background Art

Skin sagging and formation of wrinkles are typical symptoms of skin aging. As a method to address such symptoms, a facelift is performed through a process of pulling the skin in one direction, excising the excess skin, and then suturing the skin. However, since a facelift is a surgical procedure, formation of scars and occurrence of side effects are concerns.

Deviating from the surgical method, lifting treatment has been developed in which a suture harmless to the human body that has protrusions hanging thereon and is able to mechanically pull the skin is inserted into the skin to induce a natural foreign body reaction in the human body to cause collagen synthesis, angiogenesis, lipolysis, and the like and promote skin regeneration, and further, tension of a lifting suture is used to lift and fix sagging skin tissue. Because the lifting treatment is convenient and does not cause side effects compared to the surgical method, it is being performed more often.

Among the types of lifting treatments, in particular, treatment using a lifting suture for rhinoplasty to lift a drooping nose tip or correct a crooked nose or a low nose bridge allows the nose to have more volume or the nose bridge to be lifted by both ends of the lifting suture being inserted into the subcutaneous layer of the nose and the lifting suture constantly supporting the nose in a certain form. Here, the lifting suture is separately inserted into the nose bridge and the columella.

In the case in which the lifting suture is inserted into the nose and supports the shape of the nose as above, since the nose tends to return to its original shape, the lifting suture continuously receives tension over time, and in this process, the suture may move inside the nose, and one end of the lifting suture may irritate the skin, which may cause inflammation to occur or the lifting suture to protrude through the skin. In this case, the lifting suture needs to be removed, and a problem of tissue damage or the like also occurs in that process. Also, nose lifting treatment so far has limitations in terms of effects for a nose tip because only the nose bridge and columella are supported by the suture and the nose tip is not supported.

Therefore, there is an urgent need for development of a lifting suture for rhinoplasty that prevents protrusion of the lifting suture to the outside or occurrence of inflammation during rhinoplasty and addresses the existing limitations by also supporting the nose tip unlike the conventional lifting suture.

SUMMARY

Technical Problem

One aspect of the present disclosure is to provide a lifting suture for rhinoplasty and a manufacturing method thereof allowing a region disposed in a nose bridge and a region disposed in a columella to be supported by a single lifting suture.

One aspect of the present disclosure is to provide a lifting suture for rhinoplasty and a manufacturing method thereof in which a region disposed in a nose bridge and a region disposed in a columella are bent so that a predetermined angle is formed therebetween.

One aspect of the present disclosure is to provide a lifting suture for rhinoplasty in which a thickness of a connecting region disposed in a nose tip is formed to be thick.

One aspect of the present disclosure is to provide a lifting suture for rhinoplasty in which a thickness of a connecting region disposed in a nose tip is formed to gradually increase.

One aspect of the present disclosure is to provide a lifting suture for rhinoplasty in which two different kinds of cogs are disposed in each region.

One aspect of the present disclosure is to provide a lifting suture for rhinoplasty in which the shape of a cog disposed in a region corresponding to a nose bridge is formed to configure an obtuse angle relative to a central axis.

One aspect of the present disclosure is to provide a lifting suture for rhinoplasty in which two different kinds of cogs are disposed in each region.

One aspect of the present disclosure is to provide a lifting suture for rhinoplasty in which the shape of a cog disposed in a region corresponding to a nose bridge is formed to configure an obtuse angle relative to a surface.

One aspect of the present disclosure is to provide a lifting suture for rhinoplasty that further includes an extension.

One aspect of the present disclosure is to provide a lifting suture for rhinoplasty that employs an extension having various cog shapes or thicknesses.

Technical Solution

A manufacturing method of a lifting suture according to one embodiment of the present disclosure may include forming a lifting suture including a first region and a second region, each of which has cogs formed therein, and forming a connecting region by pressing the lifting suture while the first region and the second region are bent so that a first angle is formed therebetween.

A lifting suture according to the present disclosure may include a first region, a second region, and a connecting region connecting the first region and the second region, and a maximum diameter of a cross-section of the connecting region along a line perpendicular to a central axis may be longer than a maximum diameter of cross-sections of the first region and the second region.

A lifting suture according to one embodiment of the present disclosure may include a first lifting portion including one or more first cogs, and a cross-section relative to the first cog may include a first side forming an acute angle with a first direction which is formed from one side to the other side of a longitudinal direction of the lifting suture and a second side forming a right angle or an obtuse angle with the first direction.

A lifting suture according to one embodiment of the present disclosure may include a first lifting portion including one or more intagliated cogs, a cross-section relative to the intagliated cog may include a first side formed inward at a first angle from a surface of the lifting suture and a second side formed inward at a second angle from the surface, and at least one of the first angle and the second angle may be an obtuse angle.

A lifting suture according to one embodiment of the present disclosure may include two different kinds of cogs and thus have a structure advantageous for securing a fixing force necessary for lifting treatment while performing the lifting treatment for a columella and a nose bridge using a single lifting suture.

A lifting suture according to one embodiment of the present disclosure has at least one cog formed as an obtuse-angle cog inserted inward while being formed of two sides forming an obtuse angle relative to a surface of the lifting suture, and thus, even when the lifting suture is discharged from a cannula in a reverse direction, the lifting suture can be easily discharged from the cannula without being caught. Also, since at least one cog is formed as an intagliated cog, a thickness of the lifting suture may become thick, and an effect of lifting treatment can be enhanced.

A lifting suture whose first direction is defined from one side to the other side and which is utilized in plastic surgery according to one embodiment of the present disclosure may include a first lifting portion disposed at a first site of the nose of a patient, a second lifting portion disposed at a second site of the nose of the patient, and a first extension formed to extend in the first direction from the first lifting portion and disposed at the first site while having a predetermined angle with the first lifting portion.

BRIEF DESCRIPTION OF THE DRAWINGS

FIG. 3 is a view illustrating the lifting suture according to an exemplary embodiment of the present disclosure.

FIG. 16 is a view illustrating a lifting suture according to an exemplary embodiment of the present disclosure.

FIG. 18 is a view illustrating a usage example of the lifting suture according to an exemplary embodiment of the present disclosure.

FIG. 25 is a view illustrating a lifting suture according to an exemplary embodiment of the present disclosure.

FIG. 26 is a view illustrating a lifting suture according to an exemplary embodiment of the present disclosure.

DETAILED DESCRIPTION

Best Mode of the Disclosure

Figure 1:
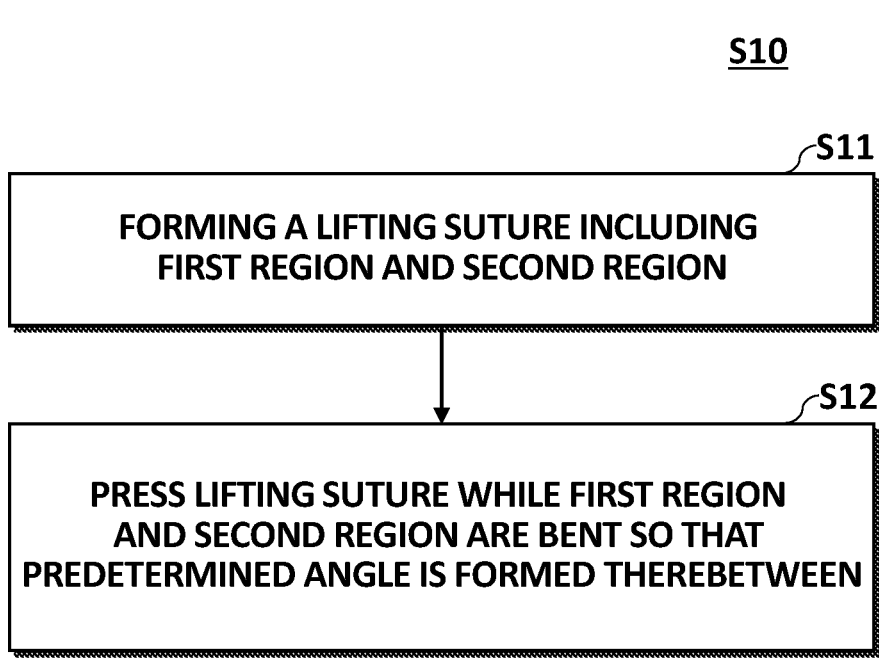
FIG. 1 is a view illustrating a manufacturing method of a lifting suture for rhinoplasty according to one embodiment of the present disclosure.

A manufacturing method of a lifting suture according to one embodiment of the present disclosure may include forming a lifting suture including a first region and a second region, each of which has cogs formed therein, and forming a connecting region by pressing the lifting suture while the first region and the second region are bent so that a first angle is formed therebetween.

Modes of the Disclosure

Hereinafter, exemplary embodiments of the present disclosure will be described in detail with reference to the accompanying drawings. Advantages and features of the present disclosure and methods of achieving the same will become apparent from the embodiments described in detail below with reference to the accompanying drawings. However, the technical spirit of the present disclosure is not limited to the following embodiments and may be implemented in various different forms. The following embodiments are provided to make the technical spirit of the present disclosure complete and to completely inform those of ordinary skill in the art to which the present disclosure pertains of the scope of the disclosure, and the technical spirit of the present disclosure is defined only by the scope of claims.

In particular, the accompanying drawings are only provided to help understanding of the present disclosure, and the present disclosure is not limited by the drawings below. Since the shapes, sizes, proportions, angles, numbers, and the like shown in the drawings are only illustrative, the present disclosure is not limited thereby.

In assigning reference numerals to components of each drawing, it should be noted that the same reference numerals are assigned to the same components wherever possible even when the components are illustrated in different drawings. Also, in describing the present disclosure, when detailed description of a known related configuration or function is determined as having the possibility of obscuring the gist of the present disclosure, the detailed description thereof will be omitted.

Unless otherwise defined, all terms including technical or scientific terms used herein have the same meaning as commonly understood by one of ordinary skill in the art to which the present disclosure pertains. Terms, such as those defined in commonly used dictionaries, should not to be construed in an idealized or overly formal sense unless expressly so defined herein. Terms used herein are for describing the embodiments and are not intended to limit the present disclosure. In the specification, a singular expression includes a plural expression unless the context clearly indicates otherwise.

Also, in describing components of the present disclosure, terms such as "first," "second," "A," "B," "(a)," and "(b)" may be used. Such terms are only for distinguishing one component from another component, and the essence, order, sequence, or the like of the corresponding component is not limited by the terms. In a case in which a certain component is described as being "connected," "coupled," or "linked" to another component, it should be understood that, although the component may be directly connected or linked to the other component, still another component may also be "connected," "coupled," or "linked" between the two components.

"Comprises" and/or "comprising" used herein do not exclude the possibility of the presence or addition of one or more other components, steps, operations, and/or elements.

A component including a common function with a component included in any one embodiment may be described using the same name in another embodiment. Unless the context clearly indicates otherwise, description made in any one embodiment may apply to another embodiment, and detailed description may be omitted within an overlapping range or a range in which those of ordinary skill in the art can clearly understand.

FIG. 1 is a view illustrating a manufacturing method of a lifting suture for rhinoplasty according to one embodiment of the present disclosure.

Referring to FIG. 1, a manufacturing method (S10) of a lifting suture for rhinoplasty may include an forming operation (S11) and a pressing operation (S12). In the forming operation (S11), a lifting suture including a first region and a second region may be injection-molded or press-molded. The lifting suture is a thread made for a surgical purpose, and in particular, a thread made for lifting treatment for lifting a nose bridge or lifting a nose tip for rhinoplasty. The lifting suture may be referred to by another name such as "lifting thread."

The first region and the second region of the lifting suture may be determined according to a position into which the lifting suture is inserted during the lifting treatment. In one example, the first region of the lifting suture may correspond to a nose bridge positioned at an upper part of the nose, and the second region of the lifting suture may correspond to a columella positioned at a lower part of the nose. The first region and the second region may be manufactured in different forms, which will be described in detail below with reference to FIG. 2.

In one embodiment, the forming of the lifting suture (S11) may include forming the lifting suture by injecting/pressing a raw material into a mold in which the first region and the second region are provided. In one example, the raw material may include one or more of polydioxanone, polylactic acid, polyglycolic acid, polycaprolactone, and a copolymer thereof, but this is only an example, and the technical spirit of the present disclosure is not limited thereto. The lifting suture injection-molded/press-molded using the raw material may have an elastic property overall. In one embodiment, the raw material may have an absorbent property and may be, when inserted into the human body, absorbed into skin tissue and disappear over time. Accordingly, since the raw material is an impermanent material, a burden on a patient that is caused by the treatment may be reduced.

In another embodiment, the lifting suture may be made of a temperature recovery material (for example, a shape-memory alloy). In this embodiment, the lifting suture may be formed to have a predetermined angle at body temperature, an angle set to be suitable for a patient may be remembered in the lifting suture, and as the lifting suture is restored to the predetermined angle inside the body, lifting treatment may be efficiently performed.

A connecting region may be formed at a portion where the first region and the second region of the lifting suture are connected. In the pressing operation (S12), the connecting region may be formed by pressing the lifting suture while the first region and the second region of the lifting suture are bent so that a predetermined angle is formed therebetween. In one embodiment, the predetermined angle may have any value in a range of 60° to 150°. In one embodiment, the pressing operation (S12) may be performed at a predetermined temperature, and in one example, the predetermined temperature may have any value between 40° C. and 60° C.

According to the technical spirit of the present disclosure, by the connecting region being formed while the predetermined angle is formed, the lifting suture may be formed to correspond to the shape of a nose. In the case in which lifting treatment for a nose is performed by utilizing the lifting suture formed according to the present disclosure, the treatment may be performed using the lifting suture having a form suitable for an angle of a nose tip of a patient, damage to internal tissue may be minimized even when the lifting suture is disposed in the internal tissue for a long period of time because a force that attempts to maintain the predetermined angle is generated and the lifting suture does not dig into the internal tissue, and an effect of rhinoplasty is maintained for a long period of time because a fixing force of the lifting suture that holds the shape of the nose is increased.

Also, conventionally, two lifting sutures are utilized to perform lifting treatment, and since the length of a nose bridge and the length of a columella are different for each patient, the lifting suture is more than necessary in some cases, and the lifting suture is insufficient in other cases. Accordingly, in some cases, the lifting suture continuously irritates the epidermis of the nose of the patient and causes inflammation, protrudes through the epidermis of the nose, or is not able to exert a force at an accurate position, which may cause a problem in the body of the patient as a result.

On the other hand, when the lifting suture formed according to the present disclosure is utilized, lifting treatment can be performed by utilizing a single lifting suture connecting a nose bridge and a columella, a problem of irritating the epidermis of a nose tip can be reduced as the connecting region between the first region and the second region is positioned at the nose tip, and since the connecting region is formed to be seated on the nose tip and thus there is no need to cut the lifting suture according to a patient at a treatment site, convenience of treatment can be significantly increased.

Figure 2:
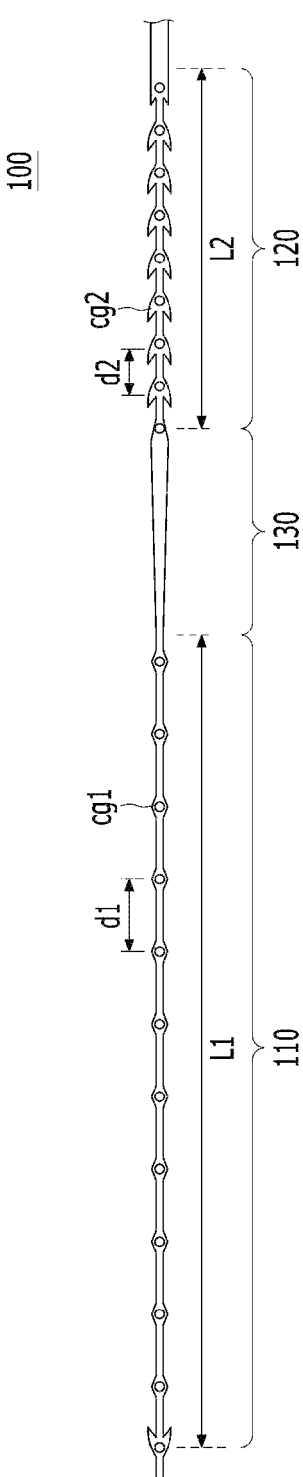
FIG. 2 is a view illustrating a lifting suture according to an exemplary embodiment of the present disclosure.

FIG. 2 is a view illustrating a lifting suture according to an exemplary embodiment of the present disclosure.

Referring to FIG. 2, a lifting suture 100 may include a first region 110, a second region 120, and a connecting region 130. In one example, the first region 110 may correspond to a nose bridge of a patient, the second region 120 may correspond to a columella of the patient, and the connecting region 130 may correspond to a nose tip of the patient. The connecting region 130 may be formed to be gradually thicker to have a cross-sectional area thicker than a cross-sectional area of the first region 110, and the connecting region 130, the first region 110, and the second region 120 may be defined by the presence/absence of cogs cg1 and cg2 and the difference in the cross-sectional area.

In one embodiment, the first region 110 may be formed to have a first length L1, and the second region 120 may be formed to have a second length L2. In one embodiment, the first length L1 of the first region 110 may be formed to be 1.4 to 3 times the second length L2 of the second region 120, and in one example, the first length L1 may be formed to be in a range of 3.5 cm to 4.5 cm, and the second length may be formed to be in a range of 1.5 cm to 2.5 cm.

According to one embodiment of the present disclosure, by the first region 110 and the second region 120 having a predetermined length ratio (in a range of 1.4:1 to 3:1), the lengths of the first region 110 and the second region 120 may be formed to have a ratio similar to a ratio of a nose bridge and a columella, and the lifting suture 100 may be formed to be suitable for body dimensions of a patient.

A plurality of first cogs cg1 may be formed in the first region 110, and a plurality of second cogs cg2 may be formed in the second region 120. In the present specification, by being formed to protrude from the lifting suture 100, the cogs cg1 and cg2 may serve to be fixed to internal tissue of the nose of a patient when the lifting suture 100 is inserted into the nose of the patient and may also be referred to as protrusions.

In one embodiment, the first cog cg1 and the second cog cg2 may be configured in different forms from each other, and the shapes of the first cog cg1 and the second cog cg2 may be formed so that a fixing force of the second cog cg2 is greater than a fixing force of the first cog cg1. The cogs cg1 and cg2 may be formed at left and right sides of the lifting suture 100 as illustrated in FIG. 2. In addition, it should be understood that, although not illustrated in FIG. 2, cogs of certain shapes may also be formed at front and rear sides of the lifting suture 100 (a surface shown in FIG. 2 and a back surface thereof), and the cogs may be formed at any position on a circumferential surface of the lifting suture 100.

The plurality of first cogs cg1 may be formed at first intervals d1 from each other. and the plurality of second cogs cg2 may be formed at second intervals d2 from each other. In one embodiment, the lifting suture 100 may be formed so that the first interval d1 of the first cogs cg1 is longer than the second interval d2 of the second cogs cg2. According to one embodiment of the present disclosure, by the first interval d1 being formed to be longer than the second interval d2, the number of cogs disposed at a nose bridge, which is longer than a columella, may be similar to the number of cogs disposed at the columella, and accordingly, the overall fixing force may be maintained.

Figure 3:
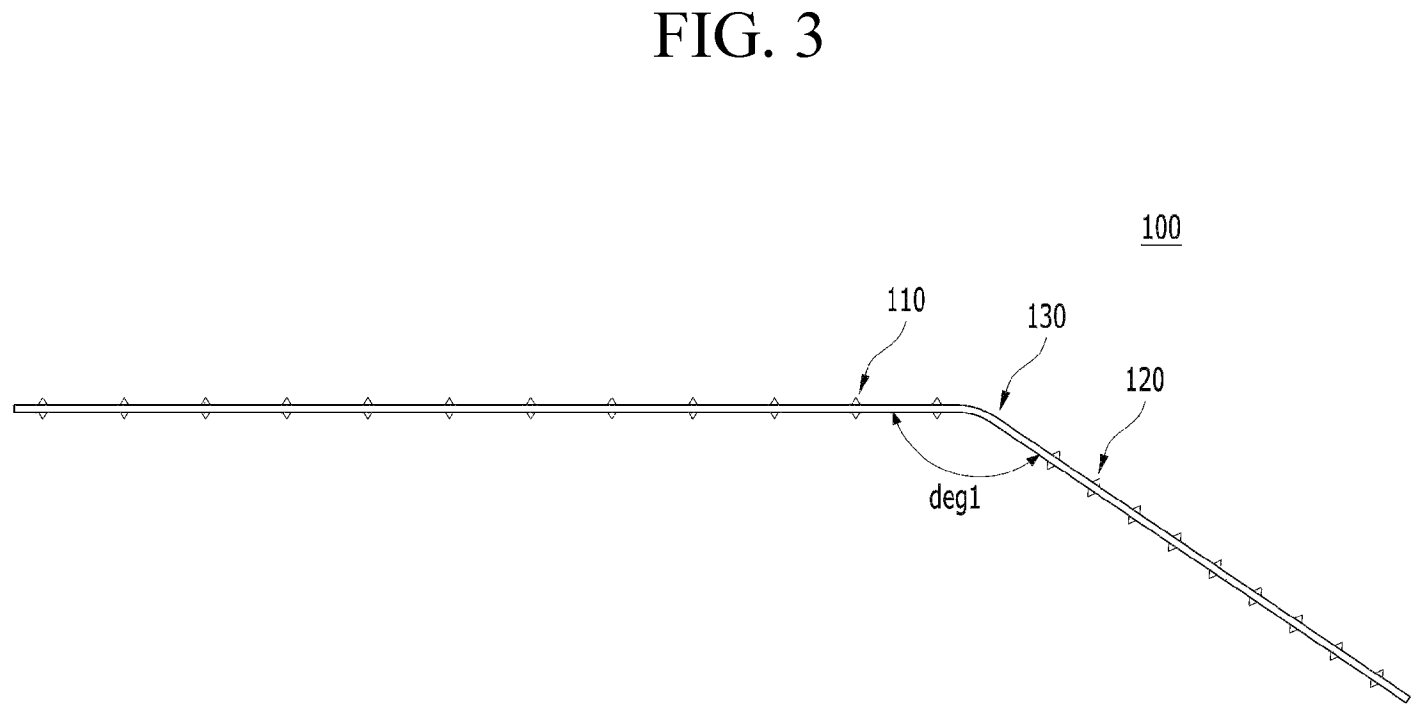

FIG. 3 is a view illustrating the lifting suture according to an exemplary embodiment of the present disclosure. Specifically, FIG. 3 may show the lifting suture of FIG. 2 that is viewed from any one side. Content overlapping with the content described above with reference to FIG. 2 will be omitted.

Referring to FIG. 3, the connecting region 130 between the first region 110 and the second region 120 may be formed while the first region 110 and the second region 120 are bent to have a first angle deg1 therebetween. In one embodiment, the connecting region 130 may be formed by pressing the lifting suture 100 while the first region 110 and the second region 120 are bent, and in another embodiment, the connecting region 130 may be formed by hardening the lifting suture 100 after heating and bending the first region 110 and the second region 120. In one embodiment, the connecting region 130 may be bent to have a predetermined radius of curvature, and as a result, the first region 110 and the second region 120 may have any angle in a range of 60° to 150° formed therebetween.

In one embodiment, the first angle deg1 may be any angle in a range of 60° to 150°. Since the lifting suture 100 is formed while the first region 110 and the second region 120 are bent to have the first angle deg1 therebetween, the lifting suture 100 may be formed in a shape suitable for the shape of the nose of a patient, and the patient's satisfaction with the treatment and convenience of treatment performed by a practitioner may be enhanced.

Although a form in which a side surface of the lifting suture 100 is bent is illustrated in FIG. 3, this is only an example, and it should be understood that the technical spirit of the present disclosure may be applied regardless of a direction in which the lifting suture 100 is bent relative to the connecting region 130.

Figure 4:
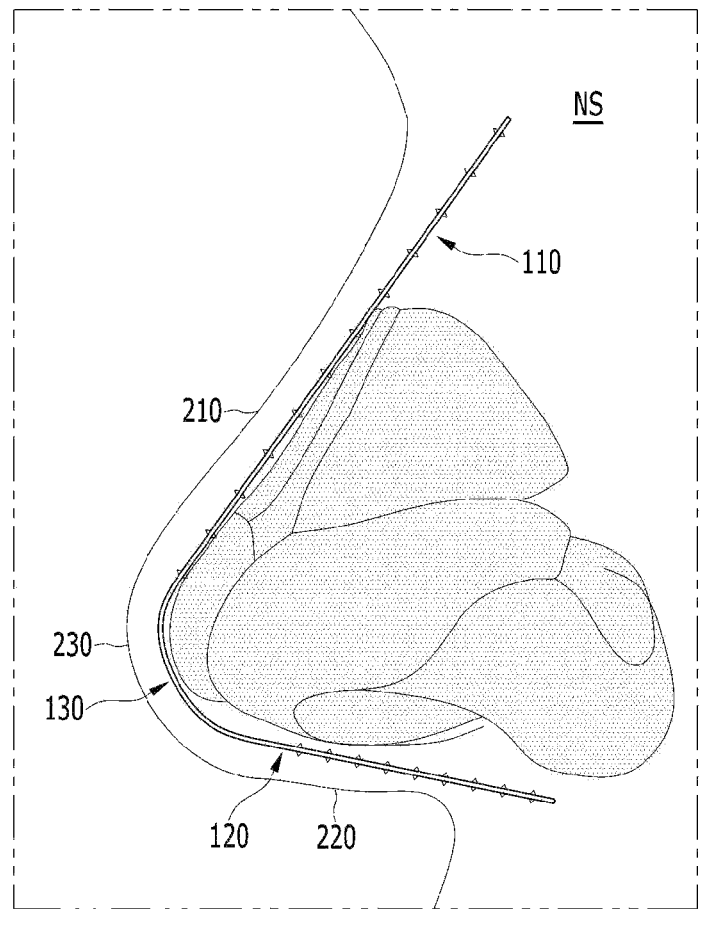
FIG. 4 is a view illustrating an embodiment in which treatment is performed by utilizing the lifting suture according to an exemplary embodiment of the present disclosure.

FIG. 4 is a view illustrating an embodiment in which treatment is performed by utilizing the lifting suture according to an exemplary embodiment of the present disclosure.

Referring to FIG. 4, a nose NS of a patient may be divided into a nose bridge part 210, a columella part 220, and a nose tip 230, and through lifting treatment, the first region 110 of the lifting suture 100 may be disposed at the nose bridge part 210, the second region 120 may be disposed at the columella part 220, and the connecting region 130 may be disposed at the nose tip 230.

Since the connecting region 130 is formed to be bent with a predetermined radius of curvature, the first region 110 and the second region 120 may have a predetermined angle formed therebetween, and accordingly, the lifting suture 100 may be formed to be suitable for the nose NS of the patient.

In one embodiment, the radius of curvature of the connecting region 130 may be changed according to a patient, and accordingly, the shape of the nose tip 230 may be shaped to be suitable for the patient.

According to the technical spirit of the present disclosure, since the connecting region 130 is formed to be bent at a predetermined angle, the lifting suture 100 may be prevented from being restored and digging into internal tissue of the nose NS or protruding through the skin, and the patient's satisfaction with the treatment may be improved.

Figure 5:
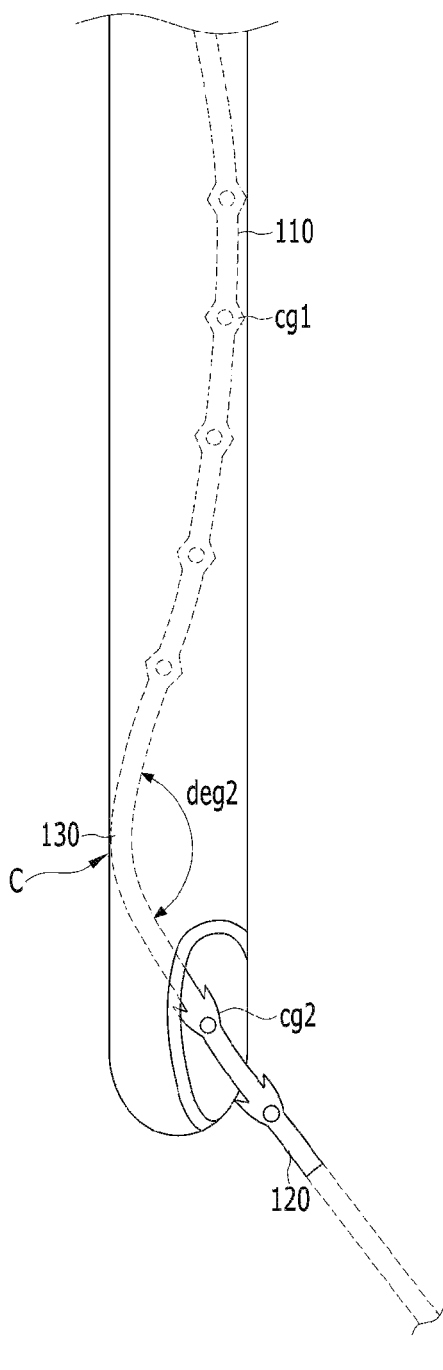
FIG. 5 is a view illustrating a state in which treatment is performed while the lifting suture according to an exemplary embodiment of the present disclosure is disposed in a cannula.

FIG. 5 is a view illustrating a state in which treatment is performed while the lifting suture according to an exemplary embodiment of the present disclosure is disposed in a cannula.

Referring to FIG. 5, the lifting suture 100 may be disposed to be inserted into a cannula C during treatment. The cannula C may be a medical tool utilized when a medical suture is inserted into tissue of a patient through the skin of the patient. During lifting treatment, a practitioner may insert the cannula C into a columella to insert the second region 120 into the columella and may move the cannula C backward to place the second region 120, fixed to tissue of the columella by the second cogs cg2, at the columella. Then, the practitioner may insert the cannula C into a nose bridge to insert the first region 110 into the nose bridge and may move the cannula C backward to place the first region 110, fixed to tissue of the nose bridge by the first cogs cg1, at the nose bridge.

To this end, in one embodiment, the first region 110 of the lifting suture 100 that is disposed at the nose bridge may be inserted into the cannula C first, and the second region 120 disposed at the columella may be inserted into the cannula C later than the first region 110.

Meanwhile, the connecting region 130 may have a second angle deg2 inside the cannula C, and since the lifting suture 100 is formed of an elastic material, the connecting region 130 may be restored to the first angle deg1, described above with reference to FIG. 3, due to the inherent elastic force of the lifting suture 100 after the lifting suture 100 is inserted into internal tissue of the nose of a patient.

According to one embodiment of the present disclosure, due to the elastic force of the lifting suture 100, as the lifting suture 100 is discharged to the nose of a patient from inside the cannula C, the angle between the first region 110 and the second region 120 of the lifting suture 100 may be restored to the predetermined angle (e.g., in a range of 60° to) 150°), and accordingly, treatment may be easily performed by utilizing the cannula C.

Figure 6:
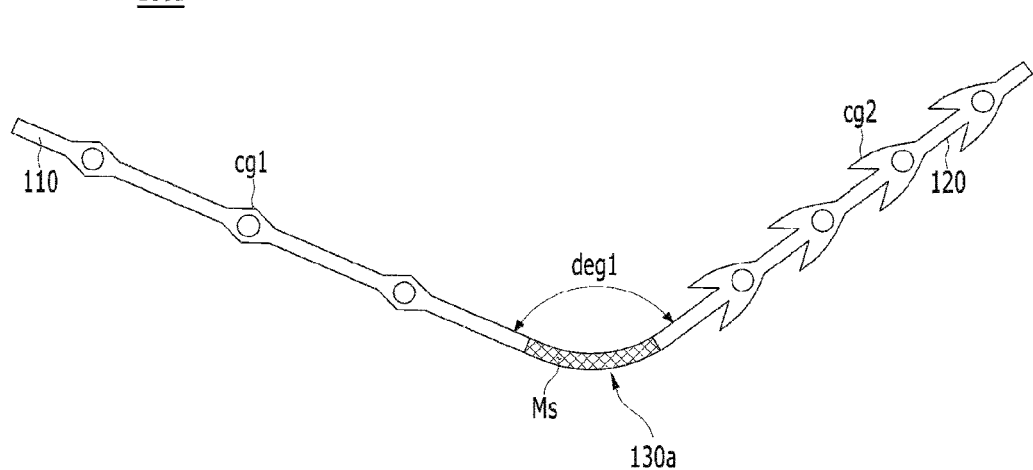
FIG. 6 is a view illustrating a lifting suture according to an exemplary embodiment of the present disclosure.

FIG. 6 is a view illustrating a lifting suture according to an exemplary embodiment of the present disclosure. Specifically, FIG. 6 illustrates an embodiment in which a connecting region 130a is configured in the form of a mesh Ms. Content overlapping with the content described above with reference to FIG. 2 will be omitted.

Referring to FIG. 6, a lifting suture 100a may include the first region 110, the second region 120, and the connecting region 130a. In one embodiment, the connecting region 130a may have the form of a mesh, and the form of the mesh Ms may be formed so that the first angle deg1 described above with reference to FIG. 3 is formed.

In the case in which a diameter of a central portion of the connecting region 130a is expanded, an adhering portion between internal tissue of the nose and the lifting suture 100a is increased, which may be effective in fixing the lifting suture 100a to the internal tissue, and a pattern of a group of rhombic or quadrangular shapes on a surface formed by the form of the mesh Ms may be supported by cartilage tissue of the nose. The form of the mesh Ms of the connecting region 130a is not limited as long as a predetermined pattern is formed thereby, and in one example, the form of the mesh Ms may be provided as a bundle of a plurality of filaments. When the connecting region 130a is provided in the form of the mesh Ms and a surface area in contact with the cartilage tissue of the nose is increased, the degree of adhesion may be increased through a foreign body reaction in the living body. Thus, the treatment effect lasts for a long time, side effects such as protrusion of the lifting suture 100a are reduced, and an area in contact with blood or bodily fluids increases, which allows rapid regeneration after the lifting suture is inserted for lifting treatment.

Also, in the case in which the connecting region 130a is formed of a structure of the mesh Ms, space is formed therein, it is very easy to introduce a biologically active substance such as hyaluronic acid (HA), polydeoxyribonucleotide (PDRN), and polynucleotide (PN), and by effectively increasing activity of a site where regeneration is most urgently needed after lifting treatment, tissue may be easily strengthened.

Figure 7:
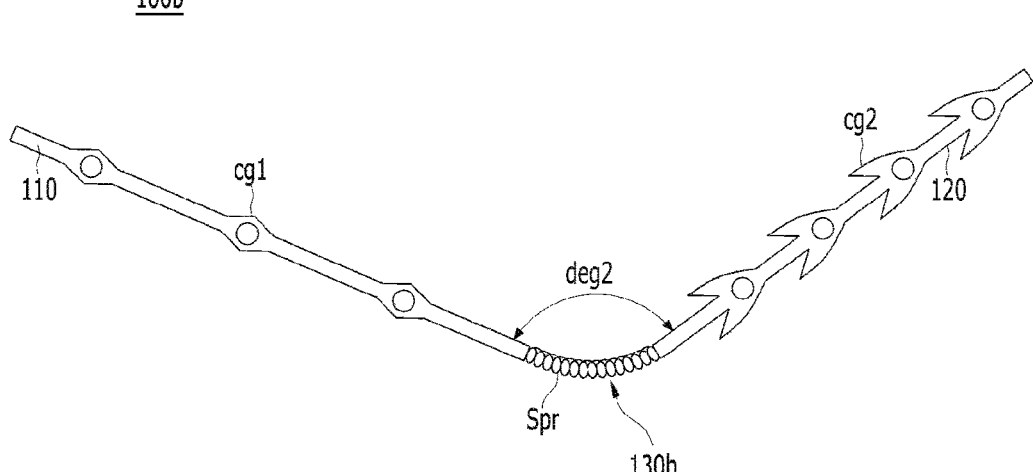
FIG. 7 is a view illustrating a lifting suture according to an exemplary embodiment of the present disclosure.

FIG. 7 is a view illustrating a lifting suture according to an exemplary embodiment of the present disclosure. Specifically, FIG. 7 illustrates an embodiment in which a connecting region 130b is configured in the form of a spring Spr. Content overlapping with the content described above with reference to FIG. 2 will be omitted.

Referring to FIG. 7, a lifting suture 100b may include the first region 110, the second region 120, and the connecting region 130b. In one embodiment, the connecting region 130b may have the form of the spring Spr, and the form of the spring Spr may be formed so that the first angle deg1 described above with reference to FIG. 3 is formed.

The form of the spring Spr may be formed through a molding or injection-molding process, and the form of the spring Spr may have high clastic force and restoration force. Accordingly, in the case in which the connecting region 130b has the form of the spring Spr, an effect of rhinoplasty may be increased due to the elasticity of the spring Spr itself in addition to the first angle deg1 of the lifting suture 100b, and the first angle deg1 formed by the first region 110 and the second region 120 may be effectively controlled.

Also, due to characteristics of the form of the spring Spr, the connecting region 130b configured in the form of the spring Spr allows a surface area of the lifting suture 100b in contact with internal tissue of the nose to increase and allows the degree of adhesion to increase through a foreign body reaction with the surrounding tissue of the nose in the living body. Thus, the effect of inserting the lifting thread may last for a long time, and side effects such as protrusion of the lifting suture 100b may be reduced.

Figure 8:
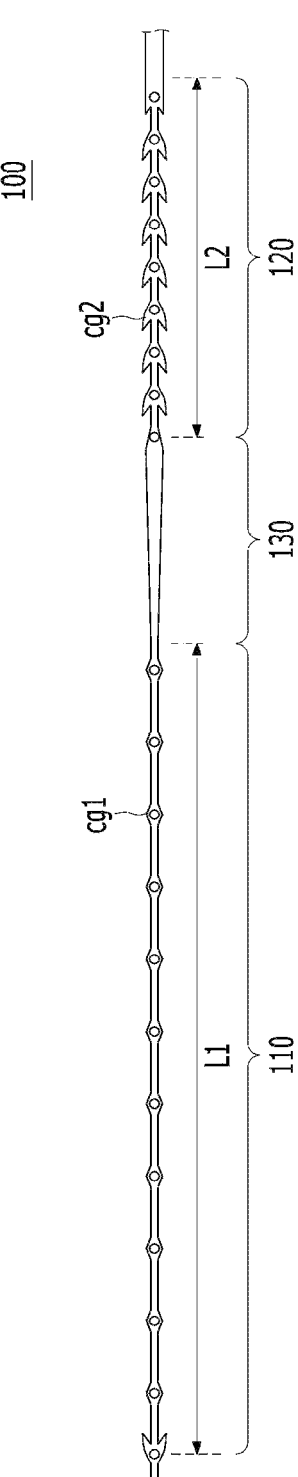
FIG. 8 is a view illustrating a lifting suture according to an exemplary embodiment of the present disclosure.

FIG. 8 is a view illustrating a lifting suture according to an exemplary embodiment of the present disclosure.

Referring to FIG. 8, the lifting suture 100 may include the first region 110, the second region 120, and the connecting region 130. In one example, the first region 110 may correspond to a nose bridge of a patient, the second region 120 may correspond to a columella of the patient, and the connecting region 130 may correspond to a nose tip of the patient. The connecting region 130, the first region 110, and the second region 120 may be defined by the presence/absence of the cogs cg1 and cg2 and a difference in a cross-sectional area.

The lifting suture is a thread made for a surgical purpose, and in particular, a thread made for lifting treatment for lifting a nose bridge or lifting a nose tip for rhinoplasty. The lifting suture may be referred to by another name such as "lifting thread."

The plurality of first cogs cg1 may be formed in the first region 110, and the plurality of second cogs cg2 may be formed in the second region 120. In the present specification, by being formed to protrude from the lifting suture 100, the cogs cg1 and cg2 may serve to be fixed to internal tissue of the nose of a patient when the lifting suture 100 is inserted into the nose of the patient and may also be referred to as protrusions. In one embodiment, the first cog cg1 and the second cog cg2 may be configured in different forms from each other, and the shapes of the first cog cg1 and the second cog cg2 may be formed so that a fixing force of the second cog cg2 is greater than a fixing force of the first cog cg1. The cogs cg1 and cg2 may be formed at left and right sides of the lifting suture 100 as illustrated in FIG. 8. In addition, it should be understood that, although not illustrated in FIG. 8, cogs of certain shapes may also be formed at front and rear sides of the lifting suture 100 (a surface shown in FIG. 8 and a back surface thereof), and the cogs may be formed at any position on the circumferential surface of the lifting suture 100.

The connecting region 130 may be formed to have a thickness that is thicker than a thickness of the first region 110 and the second region 120. In the present specification, the thickness, cross-sectional area, and cross-sectional diameter of the first region 110 and the second region 120 may be numerical values excluding the cogs cg1 and cg2 formed in the first region 110 and the second region 120.

In one embodiment, a cross-sectional area at any one position in the connecting region 130 may be formed to be wider than the cross-sectional area of the first region 110 and the second region 120. In one embodiment, a cross-sectional diameter at any one position in the connecting region 130 may be formed to be longer than the cross-sectional diameter of the first region 110 and the second region 120. The above-mentioned cross-section may be a cross-section of the connecting region 130 along a line perpendicular to the longitudinal direction of the lifting suture 100. In one embodiment, the connecting region 130 may be formed so that the cross-section thereof becomes gradually thicker from the first region 110 to the second region 120.

According to one embodiment of the present disclosure, by the connecting region 130 being formed to be thicker than the regions 110 and 120 disposed at the columella and nose bridge, pressure applied to tissue or cartilage present at the nose bridge may be reduced, and accordingly, pain felt by the patient may be reduced, deformation or damage due to the treatment may be prevented, and an effect of the treatment may be enhanced.

In one embodiment, the cross-sections of the first region 110, the second region 120, and the connecting region 130 may have an elliptical shape, and in the present specification, the maximum diameter may be the long axis of the elliptical shape.

In one embodiment, the first region 110 may be formed to have the first length L1, and the second region 120 may be formed to have the second length L2. In one embodiment, the first length L1 of the first region 110 may be formed to be 1.4 to 3 times the second length L2 of the second region 120, and in one example, the first length L1 may be formed to be in a range of 3.5 cm to 4.5 cm, the second length may be formed to be in a range of 1.5 cm to 2.5 cm, and by the first region 110 and the second region 120 having the above-mentioned length ratio and length range, the first region 110 may be suitably disposed at the nose bridge during the treatment process, and the second region 120 may be suitably disposed at the columella during the treatment process.

Figure 9:
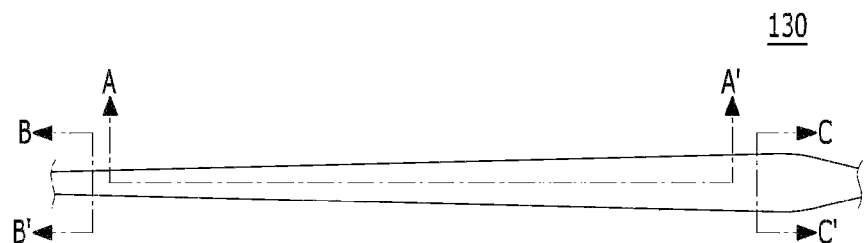
FIG. 9 is a view illustrating the lifting suture according to an exemplary embodiment of the present disclosure.

FIG. 9 is a view illustrating the lifting suture according to an exemplary embodiment of the present disclosure. Specifically, FIG. 9 is a view illustrating in detail the connecting region 130 described above with reference to FIG. 8.

Referring to FIG. 9, the connecting region 130 may include a first cross-section A-A' in the longitudinal direction, a second cross-section B-B' which is along a line perpendicular to the longitudinal direction and close to the first region 110, and a third cross-section C-C' which is along the line perpendicular to the longitudinal direction and close to the second region 120. In one example, the connecting region 130 may be connected to the first region 110 at the second cross-section B-B' and may be connected to the second region 120 at the third cross-section C-C'.

The thickness of the connecting region 130 may be formed to be gradually thinner toward the second cross-section B-B' and may be formed to be gradually thicker toward the third cross-section C-C'. Also, the cross-sectional area of the connecting region 130 may be formed to be gradually narrower toward the second cross-section B-B' and may be formed to be gradually wider toward the third cross-section C-C'. Also, the maximum cross-sectional diameter of the connecting region 130 may be formed to be gradually shorter toward the second cross-section B-B' and may be formed to be gradually longer toward the third cross-section C-C'.

In one embodiment, the diameter of the connecting region 130 may be gradually longer from the second cross-section B-B' where the connecting region 130 is connected to the first region 110 toward the third cross-section C-C' where the connecting region 130 is connected to the second region 120. Accordingly, when the connecting region 130 is disposed in the nose of a patient, a portion of the connecting region 130 that is formed to be thick may be accurately disposed at a site between cartilages, and accordingly, pressure on the cartilages positioned in the nose of the patient (for example, alar cartilages) may be reduced.

Figure 10:
FIG. 10 is a cross-sectional view of the lifting suture according to an exemplary embodiment of the present disclosure.

FIG. 10 is a cross-sectional view of the lifting suture according to an exemplary embodiment of the present disclosure. Specifically, FIG. 10 shows the cross-section of the connecting region 130 of FIG. 9 along line A-A'.

Referring to FIGS. 9 and 10, the first cross-section A-A' of the connecting region 130 along the line A-A' which is the longitudinal direction is shown. The first cross-section A-A' may include a first side A close to the first region 110 and a second side A' close to the second region 120, the first side A may have a first length d1, and the second side A' may have a second length d2. In one embodiment, the first length d1 may be formed to be shorter than the second length d2. Accordingly, the first cross-section A-A' may have a trapezoidal shape having the first side A as the upper base and the second side A' as the lower base.

Figure 11A:
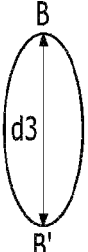
FIGS. 11A and 11B are cross-sectional views of the lifting suture according to an exemplary embodiment of the present disclosure.
Figure 11B:
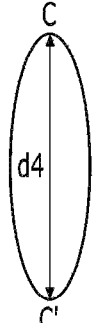

FIGS. 11A and 11B are cross-sectional views of the lifting suture according to an exemplary embodiment of the present disclosure. Specifically, FIG. 11A shows the cross-section of the connecting region 130 of FIG. 9 along line B-B', and FIG. 11B shows the cross-section of the connecting region 130 of FIG. 9 along line C-C'.

Referring to FIG. 11A, the second cross-section B-B' of the connecting region 130 at a position close to the first region 110 and along the line B-B' which is a direction perpendicular to the longitudinal direction is shown. In one embodiment, the second cross-section B-B' may be formed in an elliptical shape, and the long axis (or the maximum diameter) thereof may be formed to have a third length d3.

Referring to FIG. 11B, the third cross-section C-C' of the connecting region 130 at a position close to the second region 120 and along the line C-C' which is a direction perpendicular to the longitudinal direction is shown. In one embodiment, the third cross-section C-C' may be formed in an elliptical shape, the long axis (or the maximum diameter) thereof may be formed to have a fourth length d4, and the fourth length d4 may be longer than the third length d3.

According to one embodiment of the present disclosure, the maximum diameter of the second cross-section B-B' close to the first region 110 may be formed to be shorter than the maximum diameter of the third cross-section C-C' close to the second region 120. Accordingly, when the connecting region 130 is disposed in the nose of a patient, a portion of the connecting region 130 that is formed to be thick may be accurately disposed at a site between cartilages, and pressure applied to the cartilages and tissue positioned in the nose of the patient may be reduced.

Figure 12:
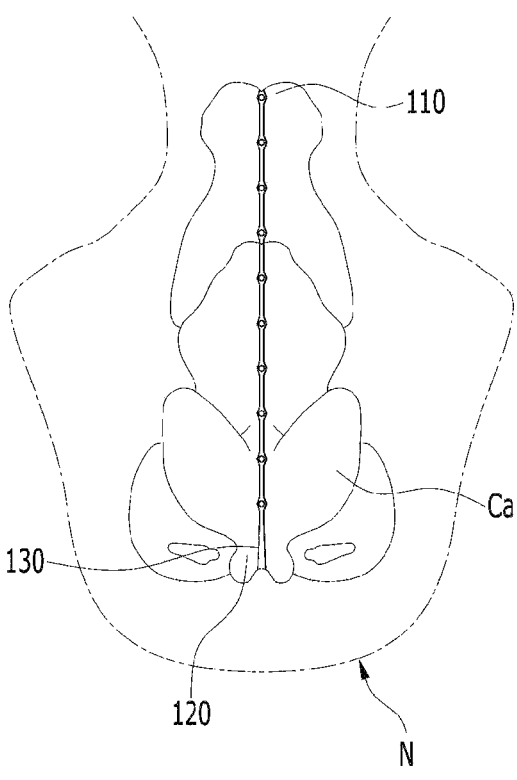
FIGS. 12 to 14 are anatomical diagrams illustrating usage examples of the lifting suture according to an exemplary embodiment of the present disclosure.
Figure 13:
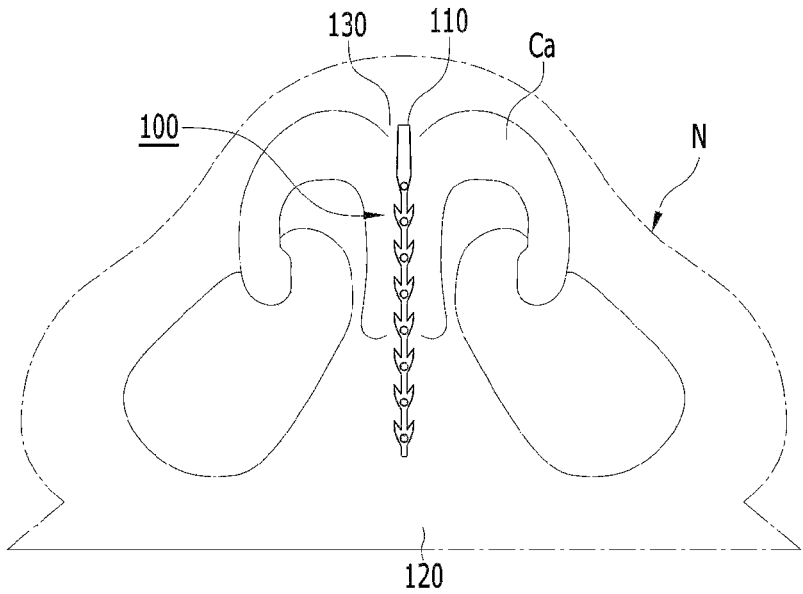
Figure 14:
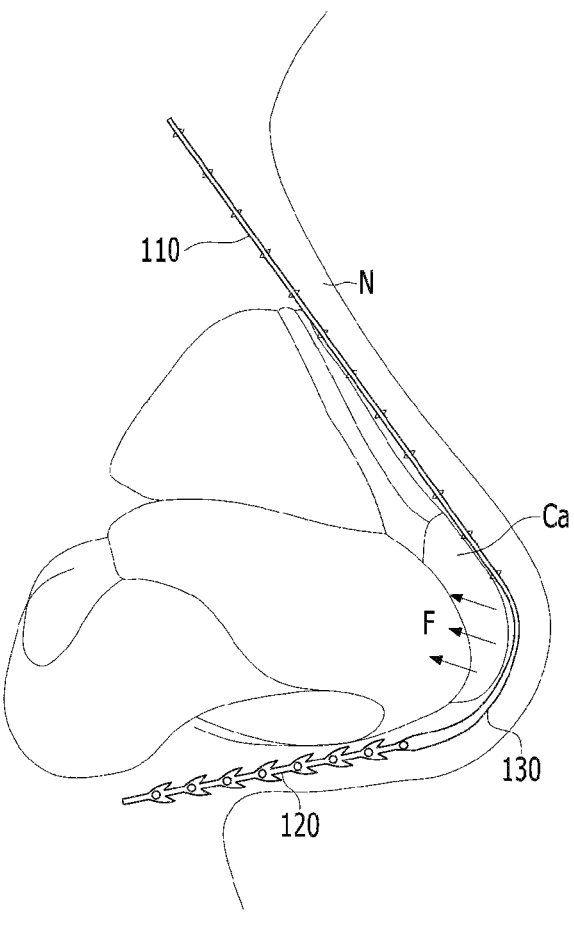

FIGS. 12 to 14 are anatomical diagrams illustrating usage examples of the lifting suture according to an exemplary embodiment of the present disclosure. Specifically, FIG. 12 is an anatomical diagram of an example in which the first region 110 of the lifting suture 100 is disposed at a nose bridge part of a nose N of a patient that is viewed so that the nose bridge is shown (for example, an anatomical diagram of the nose of the patient that is viewed from the front). Also, FIG. 13 is an anatomical diagram of an example in which the second region 120 of the lifting suture 100 is disposed at a columella part of the nose N of the patient that is viewed so that the columella is shown (for example, an anatomical diagram of the nose of the patient that is viewed from below). Also, FIG. 14 is an anatomical diagram of the nose N of the patient that is viewed from a side. Although FIGS. 12 and 13 are separately illustrated, the first region 110 illustrated in FIG. 12 and the second region 120 illustrated in FIG. 13 may be connected by the connecting region 130 in reality.

Referring to FIGS. 12 to 14, the first region 110 may cause a change in the volume and height of the nose bridge due to being disposed in internal tissue of the nose bridge, and the second region 120 may support the columella part of the nose and allow the columella part to stand straight due to being disposed in the columella site, such that the height of the columella increases, and thus rhinoplasty for increasing a nasolabial angle may be performed.

In addition, the connecting region 130 is positioned at the nose tip, and at the nose tip site, cartilages Ca (for example, alar cartilages) may be present, and the cartilages Ca may include an opening at a central site therebetween. Since the first region 110 and the second region 120 are supported by the cogs cg1 and cg2, the connecting region 130 may receive a tensile force from both sides. Due to the bent shape of the lifting suture 100, the connecting region 130 may form a net force F toward the opening of the cartilages Ca. The net force F may act on the central portion between the cartilages Ca and cause deformation of and damage to a structure between the two cartilages and may cause pain in the patient and imprecision in treatment.

The connecting region 130 according to the technical spirit of the present disclosure may have a relatively thick thickness, and accordingly, a contact area between the connecting region 130 and the cartilages Ca may increase. Since pressure that the patient receives corresponds to a value obtained by dividing the force by the surface area (P=F/A), the pressure that the patient receives may decrease with an increase in the contact area. Accordingly, in the case in which nose lifting treatment is performed by utilizing the lifting suture according to the technical spirit of the present disclosure, pressure applied to the opening between the cartilages Ca may be reduced and thus pain felt by the patient may be reduced, and since the connecting region 130 is formed to be thick, the lifting suture 100 does not easily dig into the opening between the cartilages Ca, which may minimize damage to the cartilages Ca. Also, since the nose tip is substantially supported, an effect of rhinoplasty may be enhanced.

Also, according to one embodiment of the present disclosure, the connecting region 130 may be formed to be gradually thicker toward the second region 120, and accordingly, the lifting suture 100 may be formed so that a thick portion of the connecting region 130 is accurately disposed at the opening between the cartilages Ca, and an effect of reducing the pressure applied to the opening may be maximized. Also, since the connecting region 130 is formed to be gradually thicker toward the second region 120, a support force for the second region 120 which is formed to be relatively short may be increased.

Although an example in which technical effects of the present disclosure are achieved by forming the connecting region 130 to be thick is illustrated in FIGS. 12 to 14, this is only an example, and the technical spirit of the present disclosure may also apply to an example in which the connecting region 130 is configured in the form of a mesh or an example in which the connecting region 130 is configured in the form of a coil spring. Examples of this are described in Korean Patent Application No. 10-2021-0085757 (Lifting thread for rhinoplasty using coil spring) and Korean Patent Application No. 10-2021-0085758 (Lifting thread for rhinoplasty using mesh), the contents of which are incorporated herein by reference.

Figure 15A:
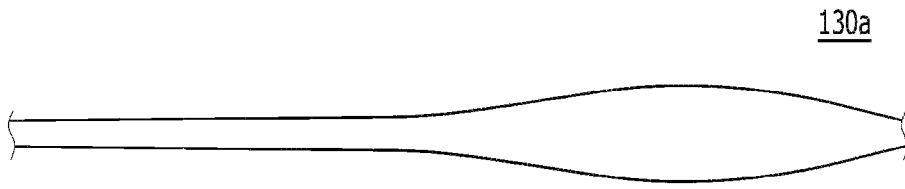
FIGS. 15A to 15C are views illustrating the connecting region according to an exemplary embodiment of the present disclosure.
Figure 15B:
Figure 15C:
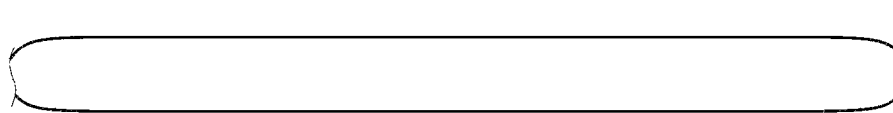

FIGS. 15A to 15C are views illustrating the connecting region according to an exemplary embodiment of the present disclosure. Content overlapping with the content described above with reference to FIGS. 1 to 14 will be omitted.

Referring to FIG. 15A, a connecting region 130a may be formed in the shape of a spoon in which a side close to the first region 110 becomes gradually thicker to have a gentle slope while a side close to the second region 120 becomes sharply thicker. In one embodiment, since the connecting region 130a is formed in the shape of a spoon, a contact area of a portion of the connecting region 130a that is positioned at the opening between the cartilages may be increased, and thus damage to the cartilages may be minimized.

Referring to FIG. 15B, a connecting region 130b may be formed in the shape of a wave that includes a plurality of thick portions and thin portions therebetween. In one embodiment, since the connecting region 130b is formed in the shape of a wave, only portions where an increase in the surface area is necessary may be formed to be thick. Also, when the lifting suture is bent to be disposed in the nose, bending may be induced at the thin portions, and thus the net force that may be applied to the nose of the patient may be minimized. Although an example in which the connecting region 130b includes two thick portions is illustrated in FIG. 15B, this is only an example, and the technical spirit of the present disclosure may also apply to an example in which the connecting region 130b includes more than two thick portions.

Referring to FIG. 15C, a connecting region 130c may be formed in the shape of a bar having the same thickness throughout. In one embodiment, since the connecting region 130c is formed in the shape of a bar that is thicker than the first region 110 and the second region 120, a manufacturing process for manufacturing the lifting suture 100 may be facilitated.

Figure 16:
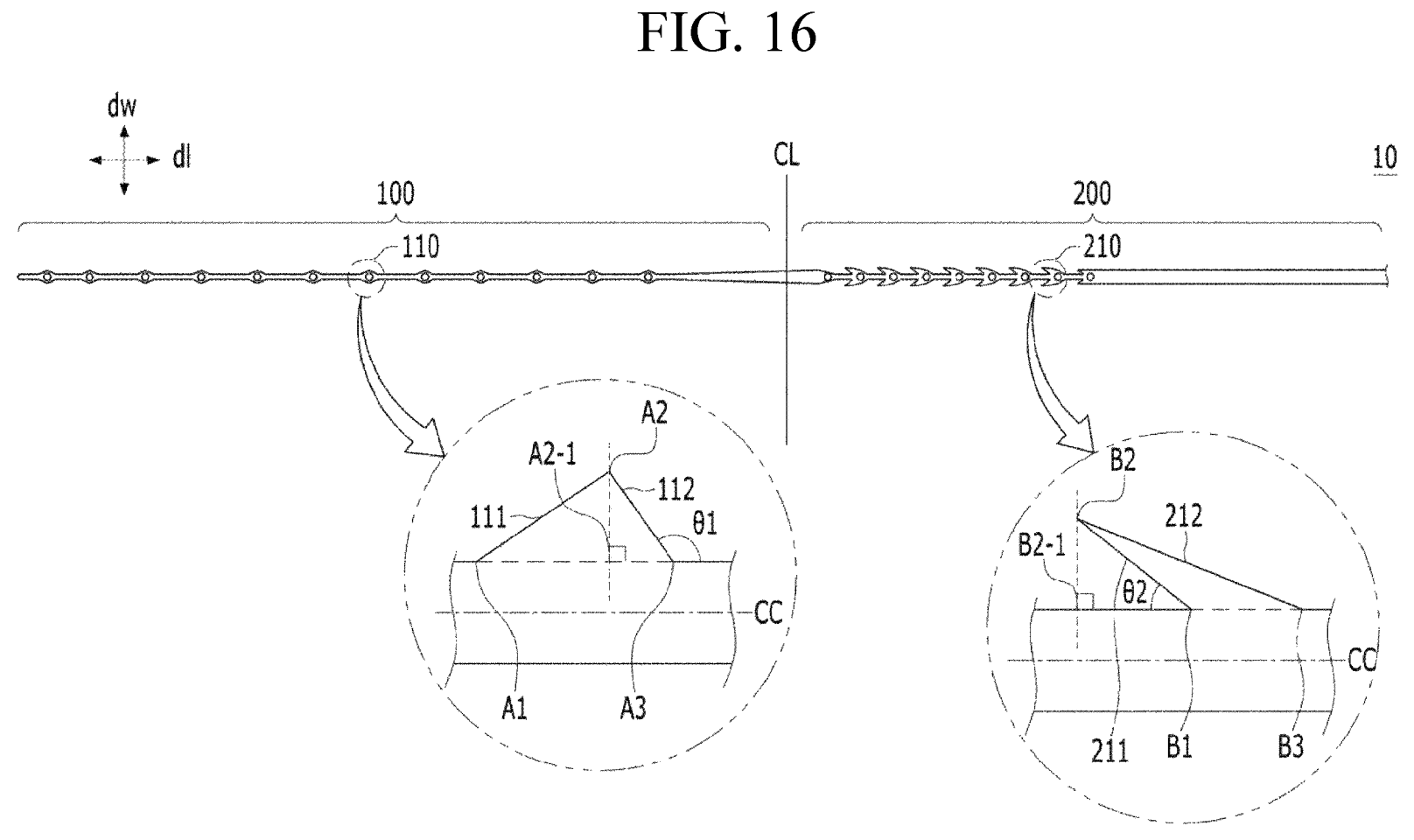

FIG. 16 is a view illustrating a lifting suture according to an exemplary embodiment of the present disclosure.

Referring to FIG. 16, a lifting suture 10 may include a first lifting portion 100 disposed at the nose bridge part of a patient and a second lifting portion 200 disposed at the columella part of the patient. The first lifting portion 100 and the second lifting portion 200 may be divided by a central axis CL. The lifting suture is a thread made for a surgical purpose, and in particular, a thread made for lifting treatment for lifting a nose bridge or lifting a nose tip for rhinoplasty. The lifting suture may be referred to by another name such as "lifting thread."

The first lifting portion 100 may include one or more first cogs 110, and the second lifting portion 200 may include one or more second cogs 210. In the present specification, by being formed to protrude from the lifting suture 10, the cogs may serve to be fixed to internal tissue of the nose of a patient when the lifting suture 10 is inserted into the nose of the patient and may also be referred to as protrusions. The cogs may be formed at left and right sides of the lifting suture 10 as illustrated in FIG. 16. In addition, it should be understood that cogs of certain shapes may also be formed at front and rear sides of the lifting suture 10 (a surface shown in FIG. 16 and a back surface thereof), and the cogs may be formed at any position on a circumferential surface of the lifting suture 10.

A cross-section of the first cog 110 of the first lifting portion 100 may be configured in a triangular shape with a relatively large vertex angle that has a side in contact with a longitudinal direction d1 of the lifting suture 10 as a base and a first side 111 and a second side 112 as the other two sides. The cross-section of the first cog 110 may include a first-first point A1 where the first side 111 and one side of the longitudinal direction d1 meet and a first-third point A3 where the second side 112 and the other side of the longitudinal direction d1 meet and may further include a first-second point A2 where the first side 111 and the second side 112 meet.

A cross-section of the second cog 210 of the second lifting portion 200 may be configured in a triangular shape with a relatively small vertex angle that has a side in contact with the longitudinal direction d1 of the lifting suture 10 as a base and a third side 211 and a fourth side 212 as the other two sides. The cross-section of the second cog 210 may include a second-first point B1 where the third side 211 and one side of the longitudinal direction d1 meet and a second-third point B3 where the fourth side 212 and the other side of the longitudinal direction d1 meet and may further include a second-second point B2 where the third side 211 and the fourth side 212 meet.

The first side 111 and the second side 112 of the first cog 110 according to one embodiment of the present disclosure may be formed leftward and rightward from the first-second point A2, and accordingly, the first cog 110 may have a gentle slope both from the one side to the other side of the longitudinal direction d1 (left to right in the example of FIG. 16) and from the other side to the one side of the longitudinal direction d1 (right to left in the example of FIG. 16). According to the technical spirit of the present disclosure, by the first cog 110 having the shape of an acute triangle that has a gentle slope in both directions, even when the lifting suture is discharged from a cannula in a reverse direction, the lifting suture can be easily discharged, which will be described in detail below with reference to FIG. 20.

Also, both the third side 211 and the fourth side 212 of the second cog 210 may be formed toward the other side from the second-second point B2 (right to left in the example of FIG. 16). Accordingly, the second cog 210 may be caught due to the second-second point B2 or a third-second point C2 in the direction opposite to the direction from the right to left. According to one embodiment of the present disclosure, since the second cog 210 is formed in the shape of a triangle with a relatively small vertex angle that may cause the second cog 210 to be caught in the direction opposite to the direction from the right to left, a fixing force in lifting treatment may be increased, which will be described in detail below with reference to FIG. 19.

For the first cog 110 to be configured in the shape of an acute triangle, a first-fourth point A2-1 at a position where a horizontal line of the lifting suture 10 meets a vertical line in a width direction dw that connects the first-second point A2 of the first cog 110 to a central axis CC may be positioned between the first-first point A1 and the first-third point A3. Also, a first angle θ1 between the second side 112 of the first cog 110 and the horizontal line of the lifting suture 10 may be an obtuse angle. The first side 111 may form an acute angle with the horizontal line in the same direction.

For the second cog 210 to be configured in the shape of a triangle with a relatively small vertex angle, a second-fourth point B2-1 at a position where the horizontal line of the lifting suture 10 meets a vertical line in the width direction dw that connects the second-second point B2 of the second cog 210 to the central axis CC may be positioned at one side (the left side in the example of FIG. 16) of the second-first point B1 and the second-third point B3. Also, a second angle θ2 between the third side 211 of the second cog 210 and the horizontal line of the lifting suture 10 may be an acute angle. The fourth side 212 may form an acute angle with the horizontal line in the same direction.

In one embodiment, a height of the first cog 110 (for example, a distance from the first-second point A2 to the first-fourth point A2-1) may be formed to be shorter than a height of the second cog 210 (for example, a distance from the second-second point B2 to the second-fourth point B2-1). Accordingly, as will be described below, the first cog 110 may be easily discharged from the cannula, and a fixing force of the second cog 210 to the nose may increase.

Also, the technical spirit of the present disclosure may also be applied to an embodiment in which the second cog 210 is disposed at the first lifting portion 100 and the first cog 110 is disposed at the second lifting portion 200 such that the first cog 110 is disposed at the columella and the second cog 210 is disposed at the nose bridge.

Figure 17:
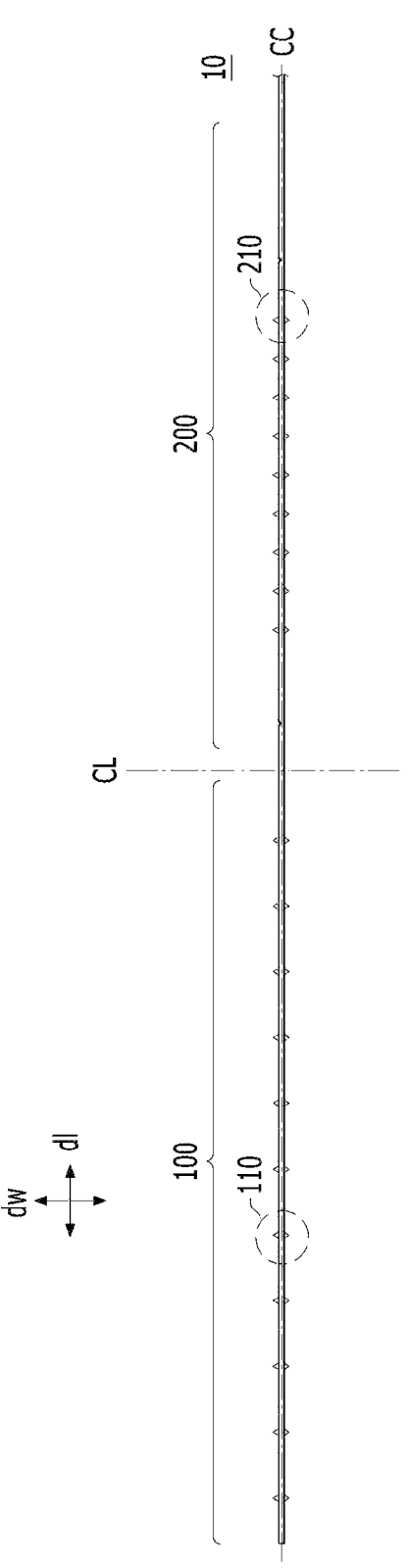
FIG. 17 is a view illustrating the lifting suture according to an exemplary embodiment of the present disclosure.

FIG. 17 is a view illustrating the lifting suture according to an exemplary embodiment of the present disclosure. Specifically, FIG. 17 may show a lateral view of the lifting suture 10 of FIG. 16.

Referring to FIG. 17, each of the first cog 110 and the second cog 210 of the lifting suture 10 may be configured to have a protrusion formed on a side surface thereof. Although a triangular or conical protrusion is illustrated as being formed on a side surface of each of the first cog 110 and the second cog 210 in FIG. 17, this is only an embodiment, and a protrusion of any other shape may be formed on the side surface of each of the first cog 110 and the second cog 210 as long as the protrusion imparts an additional fixing force. In one example, a protrusion having the shape that corresponds to the shape of each of the first cog 110 and the second cog 210 in FIG. 16 (for example, a protrusion having a triangular shape with a relatively large vertex angle or a triangular shape with a relatively small vertex angle) may be formed on the side surface of each of the first cog 110 and the second cog 210.

Although the shapes of the first cog 110 and the second cog 210 are illustrated as being different from a plan view and a lateral view according to FIGS. 16 and 17, this is only an example, and the first cog 110 and the second cog 210 may also be formed as a circular rotating body (for example, a cone) whose shape is the same from a plan view and a lateral view.

Figure 18:
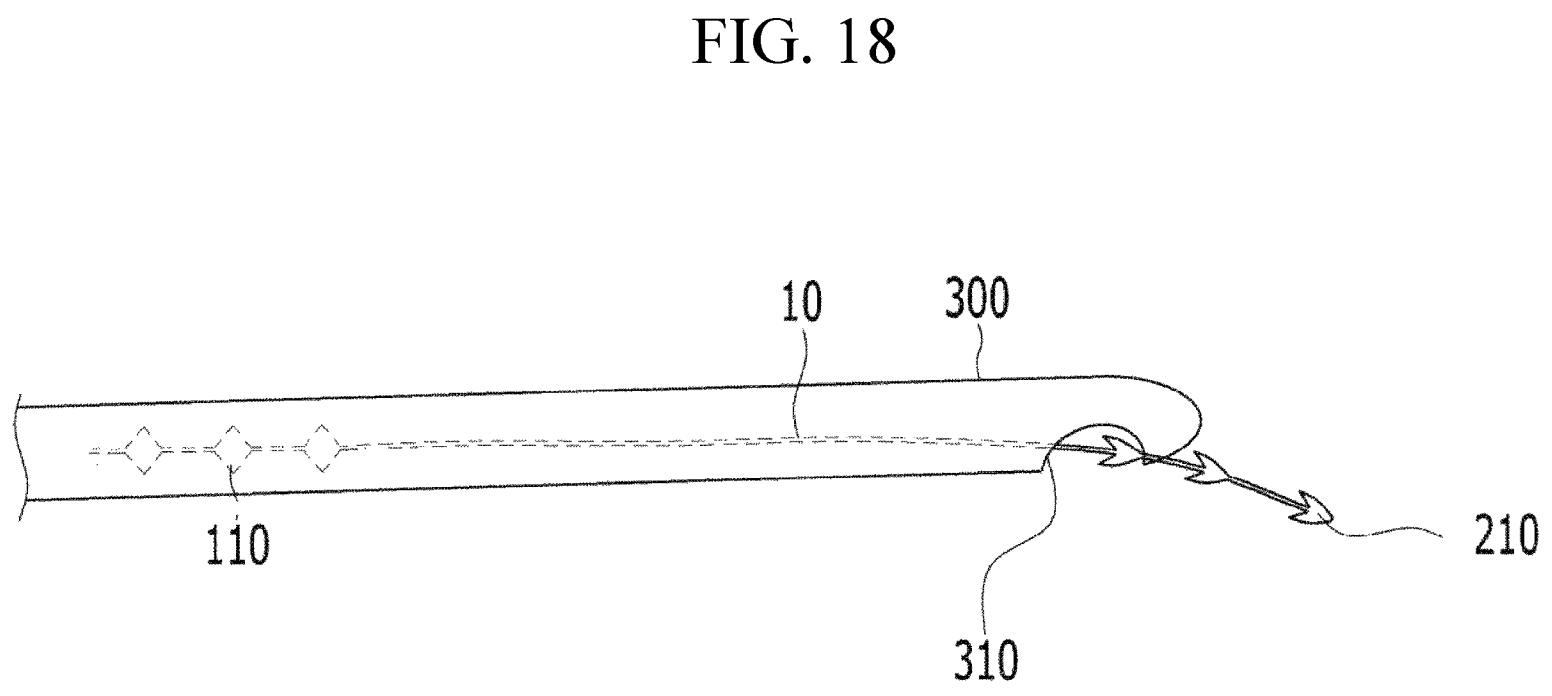

FIG. 18 is a view illustrating a usage example of the lifting suture according to an exemplary embodiment of the present disclosure. Specifically, FIG. 18 illustrates a configuration in which the lifting suture 10 is inserted into a cannula 300.

Referring to FIG. 18, the cannula 300 is a needle having an end portion formed to be round and a cannula hole 310 formed in the middle and is configured to have a structure that allows the lifting suture 10 to be inserted thereinto. Lifting treatment may be performed by a method in which the first cog 110 and the second cog 210 of the lifting suture 10 are fixed to skin tissue through an outlet 310 and the cannula 300 comes out of the skin tissue. In one embodiment, treatment for the nose bridge may be performed after treatment for the columella, and accordingly, the first cog 110 included in the first lifting portion 100 may be inserted into the cannula 300 first, and the second cog 210 included in the second lifting portion 200 may be inserted later.

Figure 19:
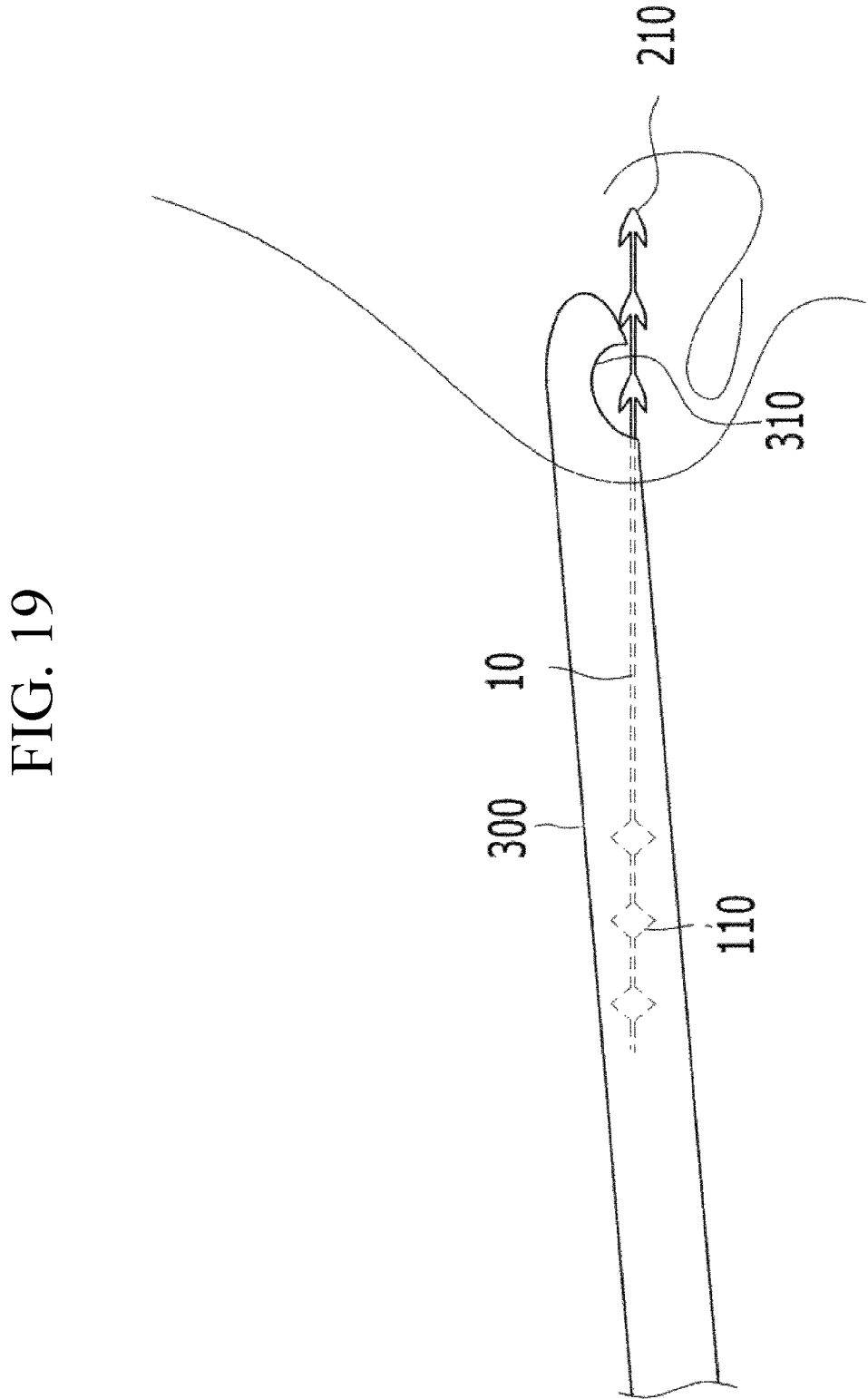
FIG. 19 is a view illustrating a usage example of the lifting suture according to an exemplary embodiment of the present disclosure.
Figure 20:
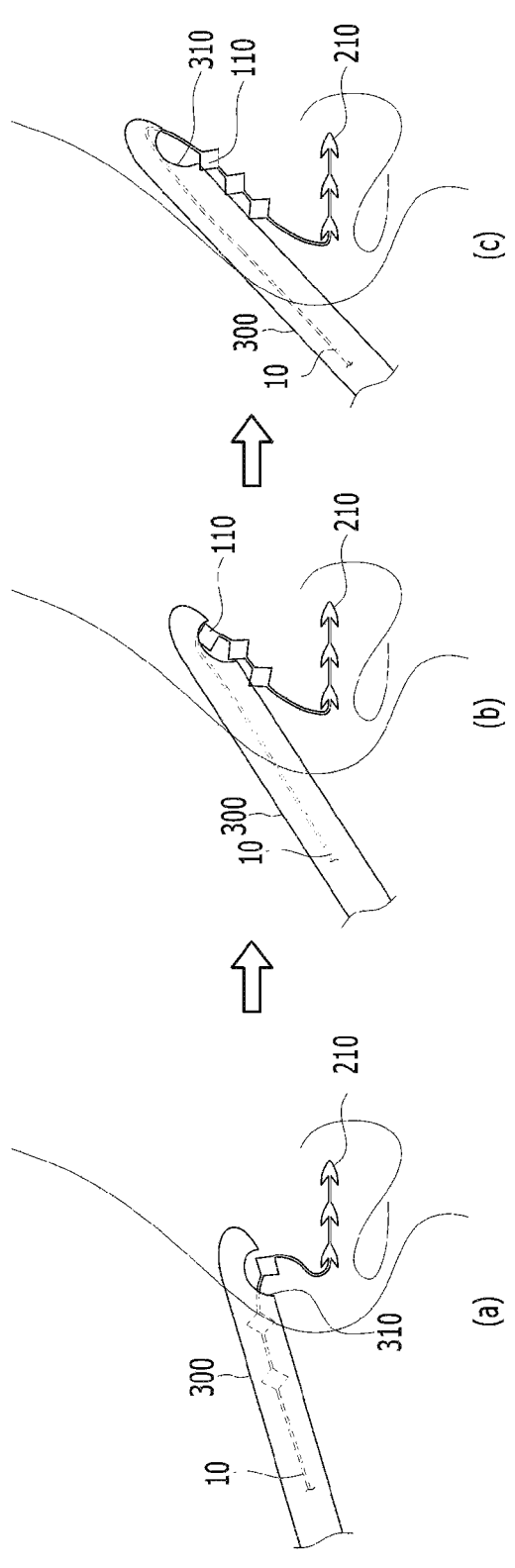
FIG. 20 is a view illustrating a usage example of the lifting suture according to an exemplary embodiment of the present disclosure.

It should be understood that, in FIGS. 18 to 20, the size of the cannula 300 may be shown with a size larger than a size of a typical cannula 300, and the number of cogs 110 and 210 included in the lifting suture 10 may be arbitrarily shown different from the actual number to facilitate the description and illustration of usage examples.

FIG. 19 is a view illustrating a usage example of the lifting suture according to an exemplary embodiment of the present disclosure. Specifically, FIG. 19 illustrates an example in which the lifting suture 10 is inserted into the columella of a patient.

Referring to FIGS. 16 and 19, a practitioner may insert the cannula 300 having the lifting suture 10 disposed therein into the columella part of a patient and may take out the inserted cannula 300 in a direction opposite to the direction of insertion. According to one embodiment of the present disclosure, since the second angle θ2 of the second cog 210 (see FIG. 16) is an acute angle, a sharp shape of the second-second point B2 of the second cog 210 (see FIG. 16) may firmly fix the second lifting portion 200 to the columella part, and in the process in which the cannula 300 is taken out, the second lifting portion 200 may be firmly disposed at the columella part of the patient through the outlet 310. Since the fourth side 212 of the second cog 210 (see FIG. 16) has a gentle slope, in the process in which the cannula 300 is taken out, the second lifting portion 200 may be easily discharged from the outlet 310.

FIG. 20 is a view illustrating a usage example of the lifting suture according to an exemplary embodiment of the present disclosure. Specifically, FIG. 20 illustrates an example in which the lifting suture 10 is inserted into the nose bridge of a patient.

Referring to FIGS. 16 and 20A, after the second lifting portion 200 of the lifting suture 10 is disposed at the columella of the patient, the practitioner may change the direction of the cannula 300 and cause the cannula 300 to enter the nose bridge. Here, since the second cog 210 is firmly fixed to the columella, the lifting suture 10 may be easily discharged from the cannula 300 even when the cannula 300 enters the nose bridge part.

Referring to FIGS. 16 and 20B, the practitioner may insert the cannula 300 into the nose bridge to place the first lifting portion 100 at the nose bridge. Here, the first lifting portion 100 is inevitably disposed in a direction opposite to a direction in which the cannula 300 advances, the first lifting portion 100 is inevitably discharged in a bent state from the outlet 310, and the first lifting portion 100 is inevitably caught between the cog of the first lifting portion 100 and the outlet 310. According to one embodiment of the present disclosure, since the first angle θ1 of the first cog 110 (see FIG. 16) is an obtuse angle, when the second cog 210 is discharged from the cannula 300, the first lifting portion 100 may be discharged from the outlet 310 along the side of the second cog 210 that has a gentle slope (for example, the fourth side 212 (see FIG. 16)), and accordingly, despite the changed direction, the first cog 110 may easily be discharged from the cannula 300.

Referring to FIGS. 16 and 20C, the practitioner may finish placing the lifting suture 10, up to the end thereof, using the cannula 300 and take out the inserted cannula 300 in the direction opposite to the direction of insertion.

Figure 21:
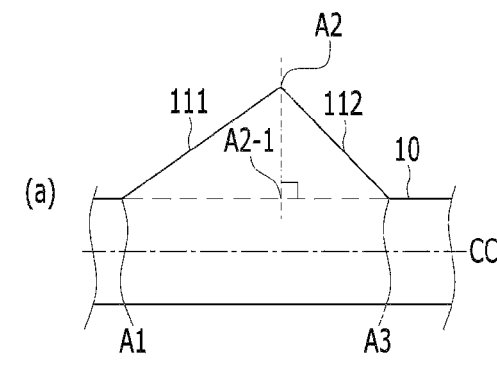
FIGS. 21 to 23 are views illustrating a cog according to an exemplary embodiment of the present disclosure.
Figure 21:
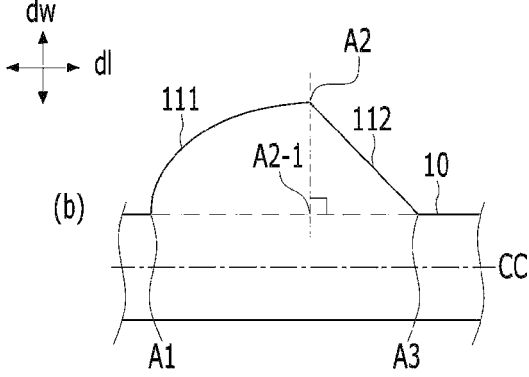
Figure 21:
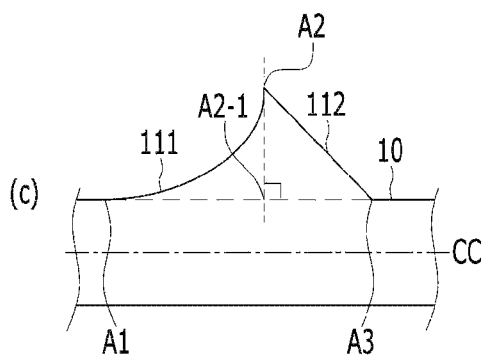
Figure 22:
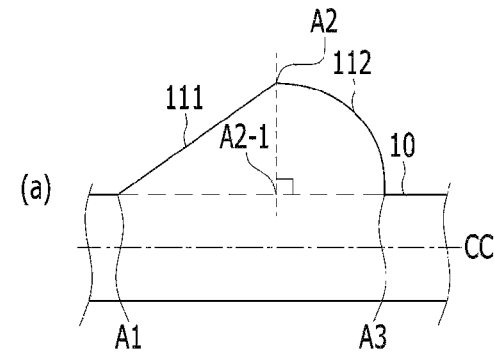
Figure 22:
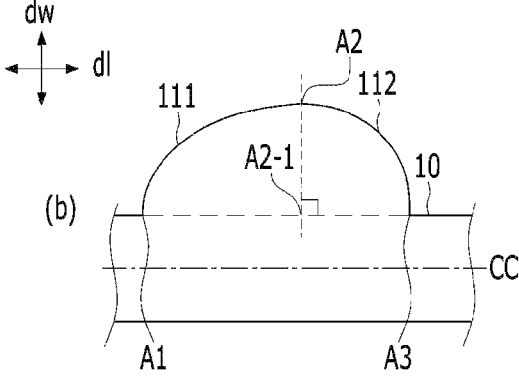
Figure 22:
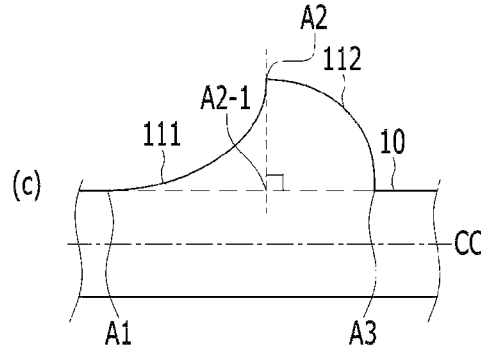
Figure 23:
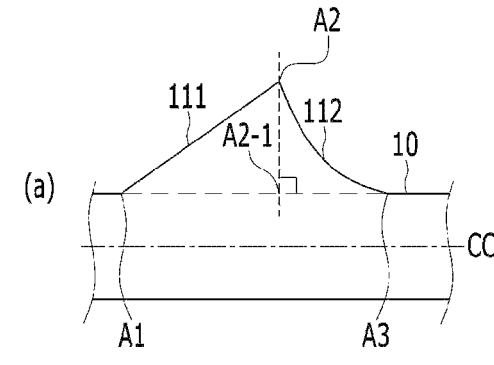
Figure 23:
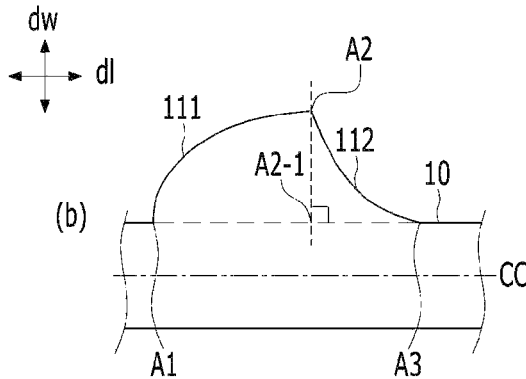
Figure 23:
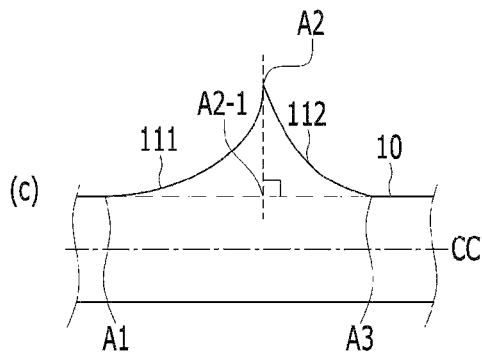

FIGS. 21 to 23 are views illustrating a cog according to an exemplary embodiment of the present disclosure. Specifically, FIGS. 21 to 23 illustrate various embodiments of the first cog 110 of FIG. 16.

Referring to FIGS. 21A to 21C, the second side 112 may be formed to have a straight line shape, and the first side 111 may be formed to have any one of a straight line shape (see FIG. 21A), a convex shape (see FIG. 21B), and a concave shape (see FIG. 21C). Even in such cases, the first side 111 and the second side 112 may be formed leftward and rightward from the first-second point A2, the angle θ1 formed between the second side 112 and the horizontal plane of the lifting suture 10 (see FIG. 16) may be an obtuse angle, and the first-fourth point A2-1 may be positioned between the first-first point A1 and the first-third point A3.

Referring to FIGS. 22A to 22C, the second side 112 may be formed to have a convex shape, and the first side 111 may be formed to have any one of a straight line shape (sec FIG. 22A), a convex shape (see FIG. 22B), and a concave shape (see FIG. 22C). Even in such cases, the first side 111 and the second side 112 may be formed leftward and rightward from the first-second point A2, the angle θ1 formed between the second side 112 and the horizontal plane of the lifting suture 10 (see FIG. 16) may be a right angle or an obtuse angle, and the first-fourth point A2-1 may be positioned between the first-first point A1 and the first-third point A3.

Referring to FIGS. 23A to 23C, the second side 112 may be formed to have a concave shape, and the first side 111 may be formed to have any one of a straight line shape (see FIG. 23A), a convex shape (see FIG. 23B), and a concave shape (see FIG. 23C). Even in such cases, the first side 111 and the second side 112 may be formed leftward and rightward from the first-second point A2, the angle θ1 formed between the second side 112 and the horizontal plane of the lifting suture 10 (see FIG. 16) may be an obtuse angle, and the first-fourth point A2-1 may be positioned between the first-first point A1 and the first-third point A3.

As in FIGS. 21 to 23, the first cog 110 may be configured in various shapes, and even in such shapes, since the first angle θ1 of the first cog 110 (see FIG. 16) is a right angle or an obtuse angle, when the second cog 210 is discharged from the cannula 300, the first lifting portion 100 may be discharged from the outlet 310 along the side of the second cog 210 that has a gentle slope (for example, the fourth side 212), and accordingly, despite the changed direction, the first cog 110 may easily be discharged from the cannula 300.

Figure 24:
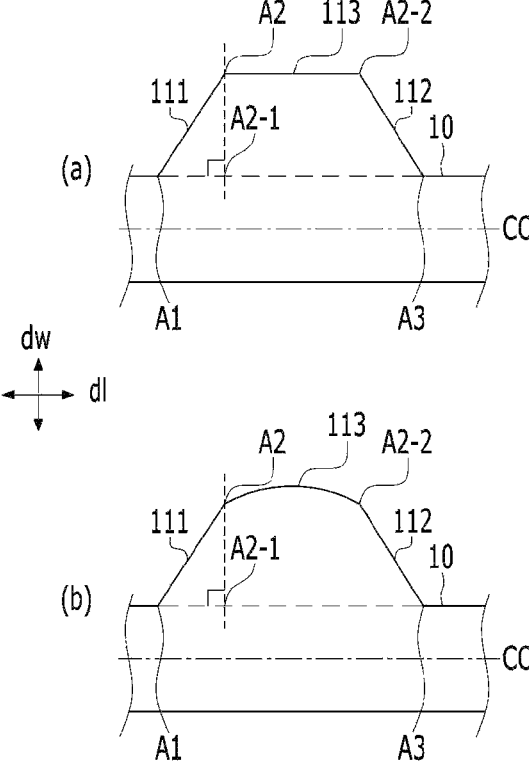
FIG. 24 is a view illustrating a cog according to an exemplary embodiment of the present disclosure.
Figure 24:
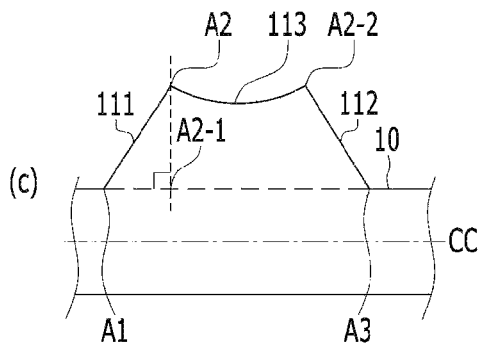

FIG. 24 is a view illustrating a cog according to an exemplary embodiment of the present disclosure. Specifically, FIG. 24 illustrates various embodiments of the first cog 110 of FIG. 16.

Referring to FIGS. 24A to 24C, the first cog 110 may be formed in the shape of a polygon with N sides (where N is a natural number that is greater than or equal to 4). In an example of FIG. 24A, the first cog 110 may have an upper side 113 formed to have a straight line shape, and even in this case, the first side 111 and the second side 112 may be formed leftward and rightward from the upper side 113, the angle θ1 formed between the second side 112 and the horizontal plane of the lifting suture 10 (see FIG. 16) may be an obtuse angle, and the first-fourth point A2-1 may be positioned between the first-first point A1 and the first-third point A3.

In an example of FIG. 24B, the first cog 110 may have an upper side 113 formed to have a convex shape, and even in this case, the first side 111 and the second side 112 may be formed leftward and rightward from the upper side 113, the angle θ1 formed between the second side 112 and the horizontal plane of the lifting suture 10 (see FIG. 16) may be an obtuse angle, and the first-fourth point A2-1 may be positioned between the first-first point A1 and the first-third point A3.

In an example of FIG. 24C, the first cog 110 may have an upper side 113 formed to have a concave shape, and even in this case, the first side 111 and the second side 112 may be formed leftward and rightward from the upper side 113, the angle θ1 formed between the second side 112 and the horizontal plane of the lifting suture 10 (see FIG. 16) may be an obtuse angle, and the first-fourth point A2-1 may be positioned between the first-first point A1 and the first-third point A3.

Figure 25:
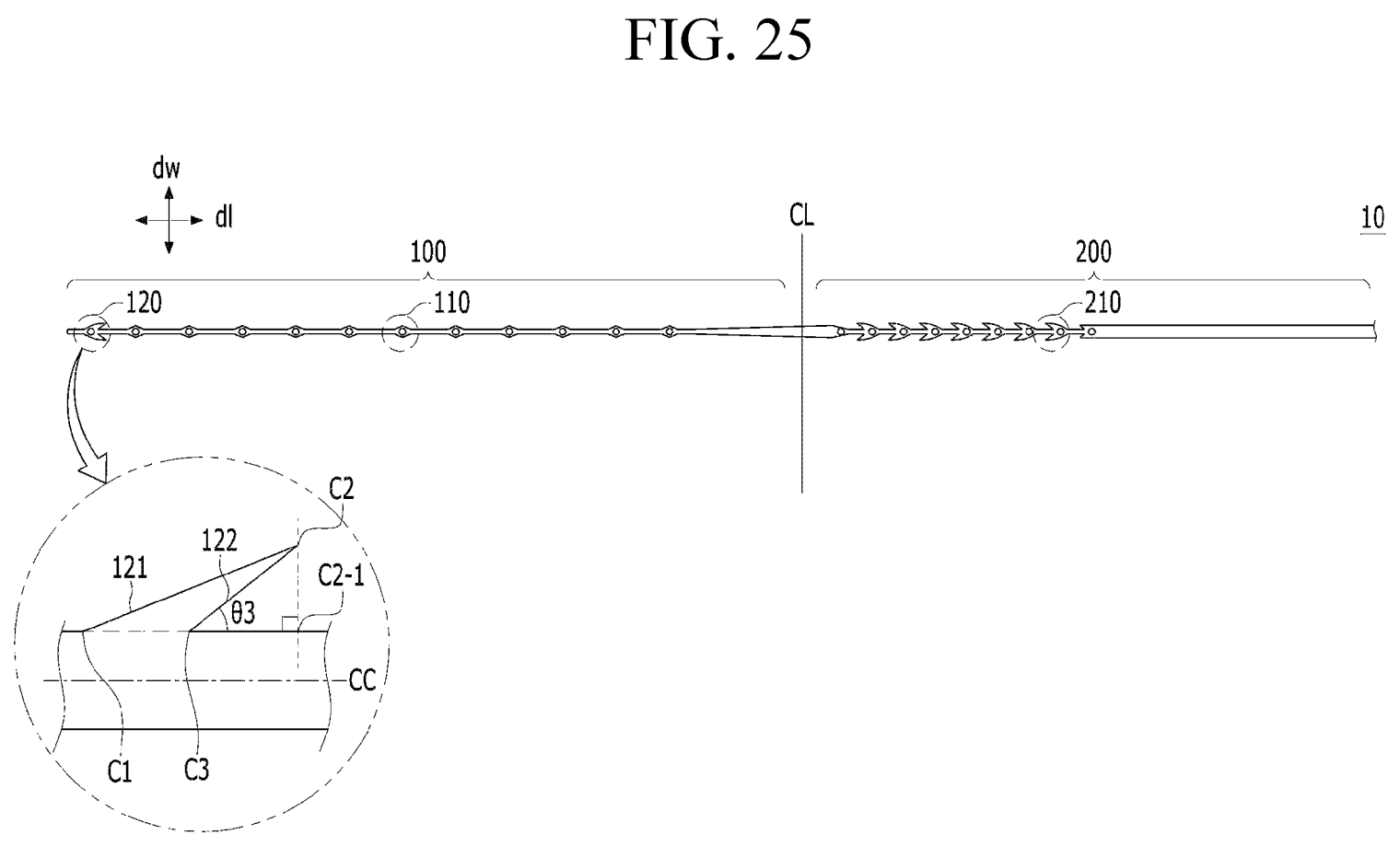

FIG. 25 is a view illustrating a lifting suture according to an exemplary embodiment of the present disclosure. FIG. 25 illustrates an embodiment in which the first lifting portion 100 includes a third cog 120. Content overlapping with the content described above with reference to FIG. 16 will be omitted.

Referring to FIG. 25, the first lifting portion 100 may include the third cog 120 provided at a tip thereof in the longitudinal direction d1 and one or more first cogs 110 sequentially provided inward from the third cog 120. In one embodiment, a cross-section of the third cog 120 may be formed in a shape similar to the shape of the cross-section of the second cog 210.

The cross-section of the third cog 120 of the first lifting portion 100 may be configured in a triangular shape with a relatively large vertex angle that has a side in contact with the longitudinal direction d1 of the lifting suture 10 as a base and a fifth side 121 and a sixth side 122 as the other two sides. The cross-section of the first cog 110 may include the first-first point A1 where the first side 111 and one side of the longitudinal direction d1 meet and the first-third point A3 where the second side 112 and the other side of the longitudinal direction d1 meet and may further include the first-second point A2 where the first side 111 and the second side 112 meet. In one embodiment, the fifth side 121 and the sixth side 122 may be symmetrical to each other.

The cross-section of the third cog 120 of the first lifting portion 100 may be configured in a triangular shape with a relatively small vertex angle that has a side in contact with the longitudinal direction d1 of the lifting suture 10 as a base and a fifth side 121 and a sixth side 122 as the other two sides. The cross-section of the third cog 120 may include a third-first point C1 where the fifth side 121 and one side of the longitudinal direction d1 meet and a third-third point C3 where the sixth side 122 and the other side of the longitudinal direction d1 meet and may further include the third-second point C2 where the fifth side 121 and the sixth side 122 meet.

Also, both the fifth side 121 and the sixth side 122 of the third cog 120 may be formed toward the one side from the third-second point C2 (right to left in the example of FIG. 16). Accordingly, the third cog 120 may be caught due to the third-second point C2 in the direction opposite to the direction from right to left. According to one embodiment of the present disclosure, since the third cog 120 is formed in the shape of a triangle with a relatively small vertex angle that may cause the third cog 120 to be caught in the direction opposite to the direction from right to left, a fixing force in lifting treatment may be increased.

For the third cog 120 to be configured in the shape of a triangle with a relatively small vertex angle, a third-fourth point C2-1 at a position where the horizontal line of the lifting suture 10 meets a vertical line in the width direction dw that connects the third-second point C2 of the third cog 120 to the central axis CC may be positioned at the other side (the right side in the example of FIG. 16) of the third-first point C1 and the third-third point C3. Also, a third angle θ3 between the sixth side 122 of the third cog 120 and the horizontal line of the lifting suture 10 may be an acute angle. The fifth side 121 may form an acute angle with the horizontal line in the same direction. Since the third angle θ3 of the third cog 120 is an acute angle, a sharp shape of the third-second point C2 of the third cog 120 may firmly fix the first lifting portion 100 to the nose bridge part, and the entire lifting suture 10 may be firmly disposed in the nose of the patient.

In one embodiment, the height of the first cog 110 (for example, the distance from the first-second point A2 to the first-fourth point A2-1) may be formed to be shorter than a height of the third cog 120 (for example, a distance from the third-second point C2 to the third-fourth point C2-1). Accordingly, as will be described below, the first cog 110 may be easily discharged from the cannula, and a fixing force of the second cog 210 and the third cog 120 to the nose may increase.

Although an example in which the first lifting portion 100 includes a single third cog 120 is illustrated in FIG. 25, this is only an example, and in another example, the first lifting portion 100 may include more than one third cog 120. Also, it should be understood that the technical spirit of the present disclosure may also apply to an example in which the first lifting portion 100 only includes the first cogs 110 without the third cog 120.

Figure 26:
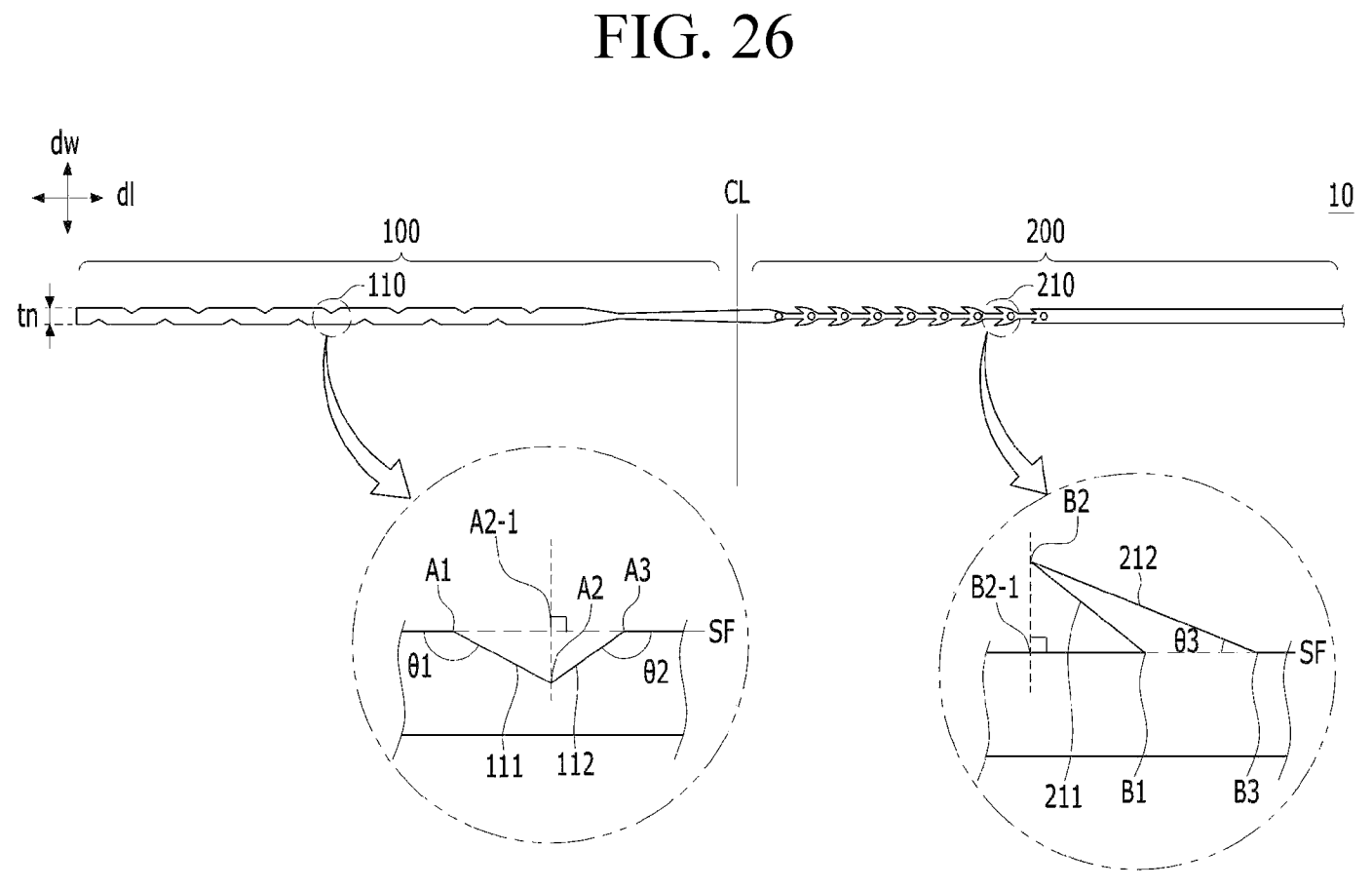

FIG. 26 is a view illustrating a lifting suture according to an exemplary embodiment of the present disclosure.

Referring to FIG. 26, the lifting suture 10 may include the first lifting portion 100 disposed at the nose bridge part of a patient and the second lifting portion 200 disposed at the columella part of the patient. The first lifting portion 100 and the second lifting portion 200 may be divided by the central axis CL. The lifting suture is a thread made for a surgical purpose, and in particular, a thread made for lifting treatment for lifting a nose bridge or lifting a nose tip for rhinoplasty. The lifting suture may be referred to by another name such as "lifting thread."

The first lifting portion 100 may include one or more intagliated cogs 110, and the second lifting portion 200 may include one or more embossed cogs 210. In the present specification, by being formed to be recessed or protrude from the lifting suture 10, the cogs may serve to be fixed to internal tissue of the nose of a patient when the lifting suture 10 is inserted into the nose of the patient and may also be referred to as protrusions. The cogs may be formed at left and right sides of the lifting suture 10 as illustrated in FIG. 26. In addition, it should be understood that cogs of certain shapes may also be formed at front and rear sides of the lifting suture 10 (a surface shown in FIG. 26 and a back surface thereof), and the cogs may be formed at any position on the circumferential surface of the lifting suture 10.

In the present specification, an intagliated cog may be a cog formed with a curve recessed inward from a surface of the lifting suture 10, instead of protruding therefrom, to induce the lifting suture 10 to be caught in internal tissue of the nose of the patient, and the embossed cog may be a cog formed with a curve protruding outward from the surface of the lifting suture 10 to induce the lifting suture 10 to be caught in internal tissue of the nose of the patient.

According to the technical spirit of the present disclosure, by the first lifting portion 100 including the intagliated cog 110, a thickness tn of the first lifting portion 100 may be thicker compared to when the embossed cog 210 is employed, and accordingly, the volume of the nose bridge of the patient may increase, and the patient's satisfaction with the treatment may increase.

A cross-section of the intagliated cog 110 of the first lifting portion 100 may include a first side 111 and a second side 112 recessed inward from a surface SF parallel to the longitudinal direction d1 of the lifting suture 10. According to one embodiment of the present disclosure, a first angle θ1 between the first side 111 and the surface SF may be an obtuse angle or a right angle, and a second angle θ2 between the second side 112 and the surface SF may be an obtuse angle or a right angle. Accordingly, the first side 111 and the second side 112 may constitute a triangle with a relatively large vertex angle with an extension line of the surface SF, and the lifting suture 10 may be easily discharged when the cannula is discharged from the first lifting portion 100 in a reverse direction, which will be described in detail below with reference to FIG. 29 and so on.

In the present specification, the shape of the cross-section of the intagliated cog 110 may be a shape of a space formed due to being recessed inward from the surface SF of the lifting suture 10 (for example, a triangular shape formed by a first-first point A1, a first-second point A2, and a first-third point A3), and the shape of a cross-section of the embossed cog 210 may be a shape of a protrusion formed due to protruding outward from the surface SF of the lifting suture

10 (for example, a triangular shape formed by a second-first point B1, a second-second point B2, and a second-third point B3.

The cross-section of the intagliated cog 110 may include the first-first point A1 where the first side 111 and one side of the longitudinal direction d1 meet and the first-third point A3 where the second side 112 and the other side of the longitudinal direction d1 meet and may further include the first-second point A2 where the first side 111 and the second side 112 meet.

The cross-section of the embossed cog 210 of the second lifting portion 200 may be configured in a triangular shape with a relatively small vertex angle that has a side in contact with the longitudinal direction d1 of the lifting suture 10 as a base and a third side 211 and a fourth side 212 as the other two sides. The cross-section of the embossed cog 210 may include the second-first point B1 where the third side 211 and one side of the longitudinal direction d1 meet and the second-third point B3 where the fourth side 212 and the other side of the longitudinal direction d1 meet and may further include the second-second point B2 where the third side 211 and the fourth side 212 meet.

The first side 111 and the second side 112 of the intagliated cog 110 according to one embodiment of the present disclosure may be formed leftward and rightward from the first-second point A2, and accordingly, the intagliated cog 110 may have a gentle slope both from the one side to the other side of the longitudinal direction d1 (left to right in the example of FIG. 26) and from the other side to the one side of the longitudinal direction d1 (right to left in the example of FIG. 26). According to the technical spirit of the present disclosure, by the intagliated cog 110 having the shape of a triangle with a relatively large vertex angle that has a gentle slope in both directions, even when the lifting suture is discharged from a cannula in a reverse direction, the lifting suture can be easily discharged, which will be described in detail below with reference to FIG. 29.

Also, both the third side 211 and the fourth side 212 of the embossed cog 210 may be formed toward the other side from the second-second point B2 (right to left in the example of FIG. 26). Accordingly, the embossed cog 210 may be caught due to the second-second point B2 or a third-second point C2 in the direction opposite to the direction from right to left. According to one embodiment of the present disclosure, since the embossed cog 210 is formed in the shape of a triangle with a relatively small vertex angle that may cause the embossed cog 210 to be caught in the direction opposite to the direction from right to left, a fixing force in lifting treatment may be increased, which will be described in detail below with reference to FIG. 28.

For the intagliated cog 110 to be configured in the shape of a triangle with a relatively large vertex angle, a first-fourth point A2-1 at a position where an extension line of the surface SF of the lifting suture 10 meets a vertical line in the width direction dw that connects the first-second point A2 of the intagliated cog 110 to the central axis may be positioned between the first-first point A1 and the first-third point A3.

For the embossed cog 210 to be configured in the shape of a triangle with a relatively small vertex angle, a second-fourth point B2-1 at a position where the horizontal line of the lifting suture 10 meets a vertical line in the width direction dw that connects the second-second point B2 of the embossed cog 210 to the central axis may be positioned at one side (the left side in the example of FIG. 26) of the second-first point B1 and the second-third point B3. Also, a third angle θ3 between the third side 211 of the embossed cog 210 and the horizontal line of the lifting suture 10 may be an acute angle. The fourth side 212 may form an acute angle with the horizontal line in the same direction.

Also, the technical spirit of the present disclosure may also be applied to an embodiment in which the embossed cog 210 is disposed at the first lifting portion 100 and the intagliated cog 110 is disposed at the second lifting portion 200 such that the intagliated cog 110 is disposed at the columella and the embossed cog 210 is disposed at the nose bridge.

Figure 27:
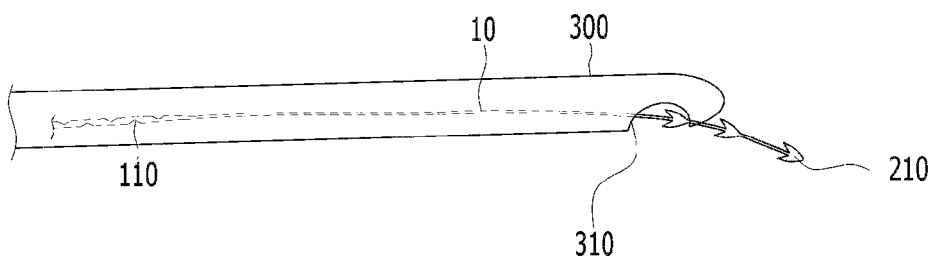
FIG. 27 is a view illustrating a usage example of the lifting suture according to an exemplary embodiment of the present disclosure.

FIG. 27 is a view illustrating a usage example of the lifting suture according to an exemplary embodiment of the present disclosure. Specifically, FIG. 27 illustrates a configuration in which the lifting suture 10 is inserted into a cannula 300.

Referring to FIG. 27, the cannula 300 is a needle having an end portion formed to be round and a cannula hole 310 formed in the middle and is configured to have a structure that allows the lifting suture 10 to be inserted thereinto. Lifting treatment may be performed by a method in which the intagliated cog 110 and the embossed cog 210 of the lifting suture 10 are fixed to skin tissue through an outlet 310 and the cannula 300 comes out of the skin tissue. In one embodiment, treatment for the nose bridge may be performed after treatment for the columella, and accordingly, the intagliated cog 110 included in the first lifting portion 100 may be inserted into the cannula 300 first, and the embossed cog 210 included in the second lifting portion 200 may be inserted later.

Figure 28:
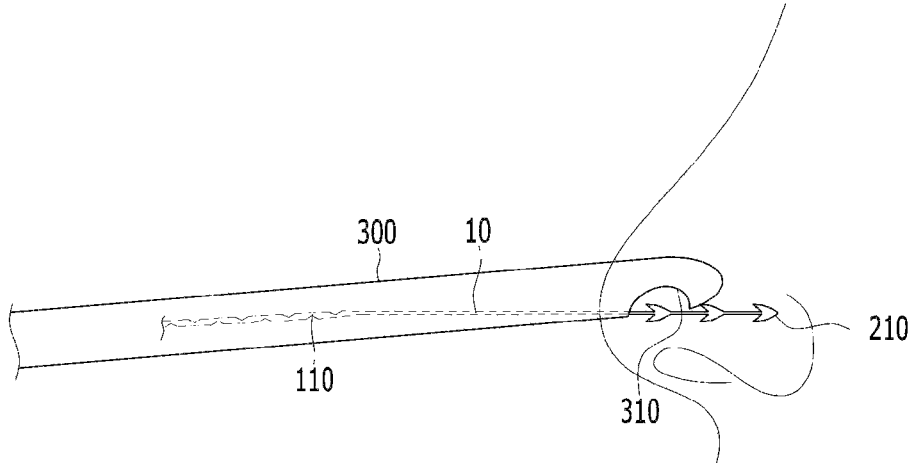
FIG. 28 is a view illustrating a usage example of the lifting suture according to an exemplary embodiment of the present disclosure.
Figure 29:
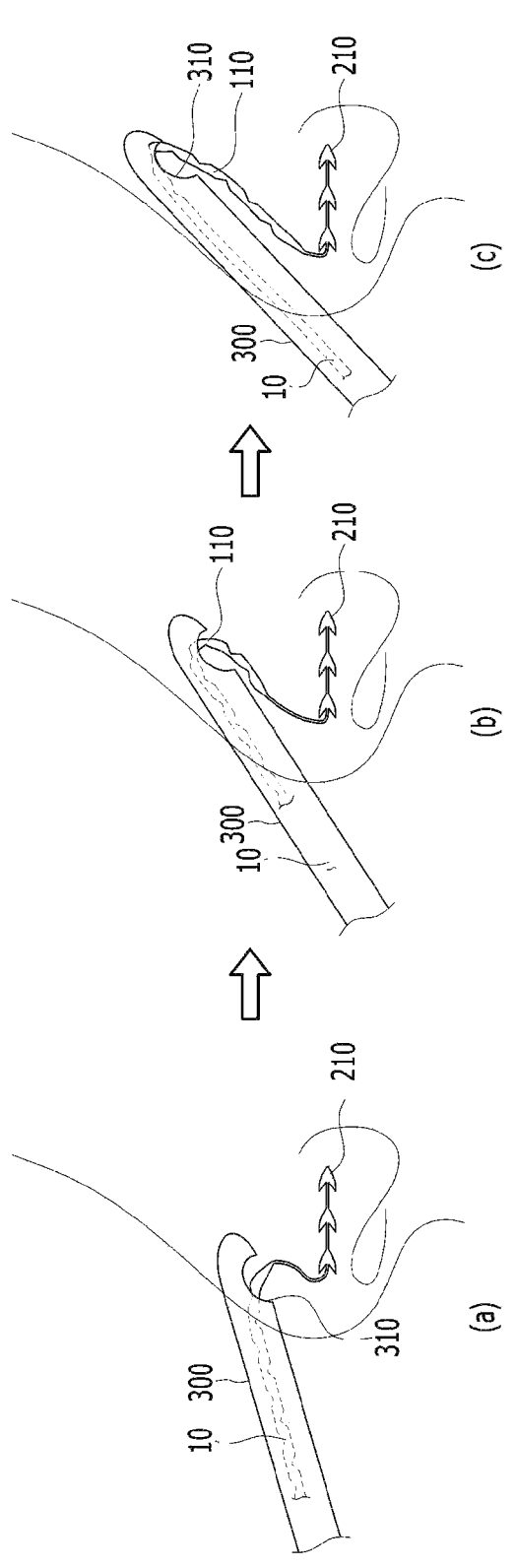
FIG. 29 is a view illustrating a usage example of the lifting suture according to an exemplary embodiment of the present disclosure.

It should be understood that, in FIGS. 27 to 29, the size of the cannula 300 may be shown with a size larger than a size of a typical cannula 300, and the number of cogs 110 and 210 included in the lifting suture 10 may be arbitrarily shown different from the actual number to facilitate the description and illustration of usage examples.

FIG. 28 is a view illustrating a usage example of the lifting suture according to an exemplary embodiment of the present disclosure. Specifically, FIG. 28 illustrates an example in which the lifting suture 10 is inserted into the columella of a patient.

Referring to FIGS. 26 and 28, a practitioner may insert the cannula 300 having the lifting suture 10 disposed therein into the columella part of a patient and may take out the inserted cannula 300 in a direction opposite to the direction of insertion. According to one embodiment of the present disclosure, since the third angle θ3 of the embossed cog 210 (see FIG. 26) is an acute angle, a sharp shape of the second-second point B2 of the embossed cog 210 (see FIG. 26) may firmly fix the second lifting portion 200 to the columella part, and in the process in which the cannula 300 is taken out, the second lifting portion 200 may be firmly disposed at the columella part of the patient through the outlet 310. Since the fourth side 212 of the embossed cog 210 (see FIG. 26) has a gentle slope, in the process in which the cannula 300 is taken out, the second lifting portion 200 may be easily discharged from the outlet 310.

FIG. 29 is a view illustrating a usage example of the lifting suture according to an exemplary embodiment of the present disclosure. Specifically, FIG. 29 illustrates an example in which the lifting suture 10 is inserted into the nose bridge of a patient.

Referring to FIGS. 26 and 29A, after the second lifting portion 200 of the lifting suture 10 is disposed at the columella of the patient, the practitioner may change the direction of the cannula 300 and cause the cannula 300 to enter the nose bridge. Here, since the embossed cog 210 is firmly fixed to the columella, the lifting suture 10 may be easily discharged from the cannula 300 even when the cannula 300 enters the nose bridge part.

Referring to FIGS. 26 and 29B, the practitioner may insert the cannula 300 into the nose bridge to place the first lifting portion 100 at the nose bridge. Here, the first lifting portion 100 is inevitably disposed in a direction opposite to a direction in which the cannula 300 advances, the first lifting portion 100 is inevitably discharged in a bent state from the outlet 310, and the first lifting portion 100 is inevitably caught between the cog of the first lifting portion 100 and the outlet 310. According to one embodiment of the present disclosure, since the first angle θ1 of the intagliated cog 110 (see FIG. 26) is an obtuse angle, when the embossed cog 210 is discharged from the cannula 300, the first lifting portion 100 may be discharged from the outlet 310 along the side of the embossed cog 210 that has a gentle slope (for example, the fourth side 212 (see FIG. 26)), and accordingly, despite the changed direction, the intagliated cog 110 may easily be discharged from the cannula 300.

Referring to FIGS. 26 and 29C, the practitioner may finish placing the lifting suture 10, up to the end thereof, using the cannula 300 and take out the inserted cannula 300 in the direction opposite to the direction of insertion. Here, since the lifting suture 10 includes the intagliated cog 110, the thickness of the first lifting portion 100 disposed in the patient may be thick, and accordingly, the volume of the nose bridge of the patient may increase, and the patient's satisfaction with the treatment may increase.

Figure 30:
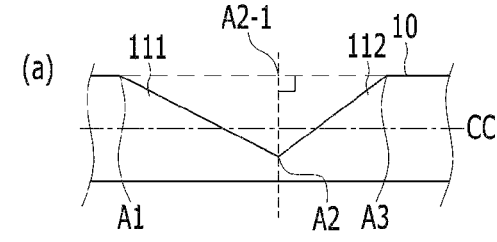
FIGS. 30 to 32 are views illustrating an intagliated cog according to an exemplary embodiment of the present disclosure.
Figure 30:
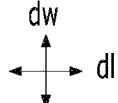
Figure 30:
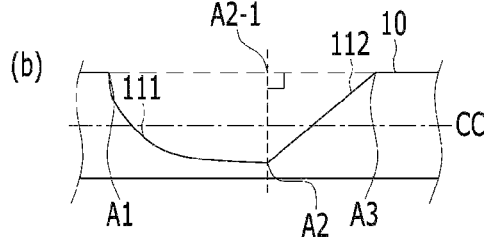
Figure 30:
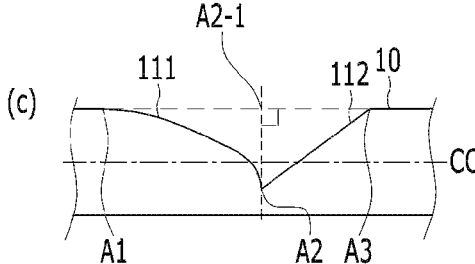
Figure 31:
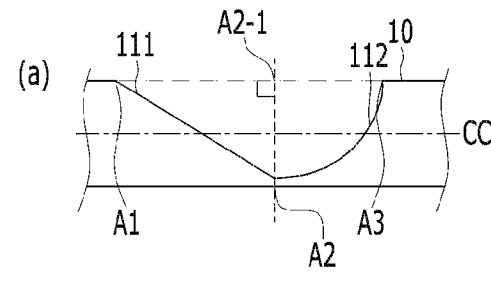
Figure 31:
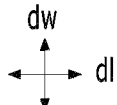
Figure 31:
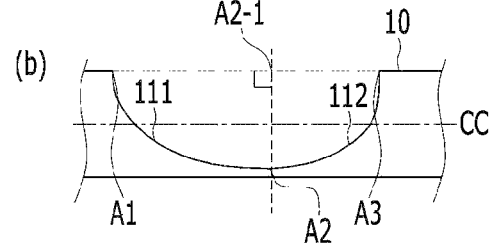
Figure 31:
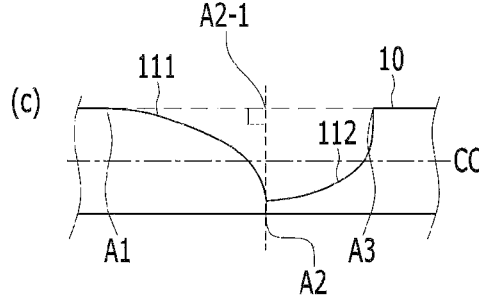
Figure 32:
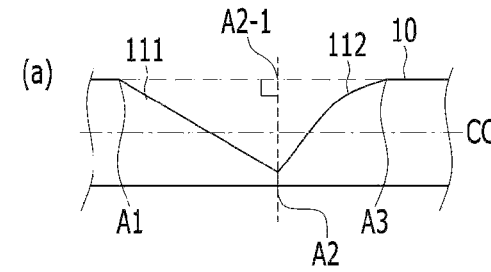
Figure 32:
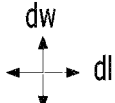
Figure 32:
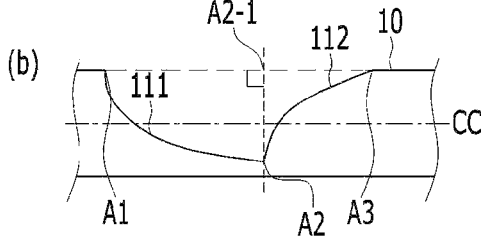
Figure 32:
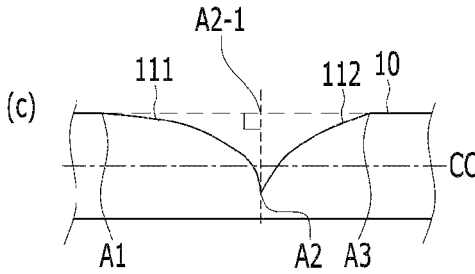

FIGS. 30 to 32 are views illustrating an intagliated cog according to an exemplary embodiment of the present disclosure. Specifically, FIGS. 30 to 32 illustrate various embodiments of the intagliated cog 110 of FIG. 26.

Referring to FIGS. 30A to 30C, the second side 112 may be formed to have a straight line shape, and the first side 111 may be formed to have any one of a straight line shape (see FIG. 30A), a convex shape (see FIG. 30B), and a concave shape (see FIG. 30C). Even in such cases, the first side 111 and the second side 112 may be formed leftward and rightward from the first-second point A2, the angle θ1 formed between the second side 112 and the surface of the lifting suture 10 (see FIG. 26) may be an obtuse angle, and the first-fourth point A2-1 may be positioned between the first-first point A1 and the first-third point A3.

Referring to FIGS. 31A to 31C, the second side 112 may be formed to have a convex shape, and the first side 111 may be formed to have any one of a straight line shape (see FIG. 31A), a convex shape (see FIG. 31B), and a concave shape (see FIG. 31C). Even in such cases, the first side 111 and the second side 112 may be formed leftward and rightward from the first-second point A2, the angle θ1 formed between the second side 112 and the surface of the lifting suture 10 (see FIG. 26) may be a right angle or an obtuse angle, and the first-fourth point A2-1 may be positioned between the first-first point A1 and the first-third point A3.

Referring to FIGS. 32A to 32C, the second side 112 may be formed to have a concave shape, and the first side 111 may be formed to have any one of a straight line shape (see FIG. 32A), a convex shape (see FIG. 32B), and a concave shape (see FIG. 32C). Even in such cases, the first side 111 and the second side 112 may be formed leftward and rightward from the first-second point A2, the angle θ1 formed between the second side 112 and the surface of the lifting suture 10 (see FIG. 26) may be an obtuse angle, and the first-fourth point A2-1 may be positioned between the first-first point A1 and the first-third point A3.

As in FIGS. 30 to 32, the intagliated cog 110 may be configured in various shapes, and even in such shapes, since the first angle θ1 of the intagliated cog 110 (see FIG. 26) is a right angle or an obtuse angle, when the embossed cog 210 is discharged from the cannula 300, the first lifting portion 100 may be discharged from the outlet 310 along the side of the embossed cog 210 that has a gentle slope (for example, the fourth side 212), and accordingly, despite the changed direction, the intagliated cog 110 may easily be discharged from the cannula 300.

Figure 33:
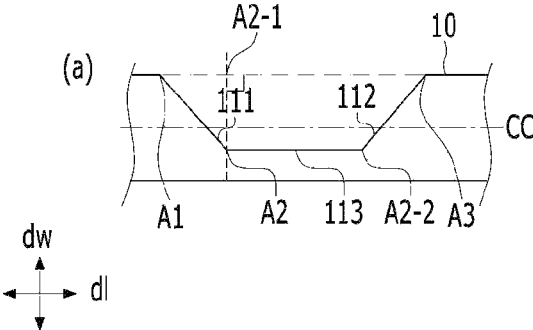
FIG. 33 is a view illustrating a cog according to an exemplary embodiment of the present disclosure.
Figure 33:
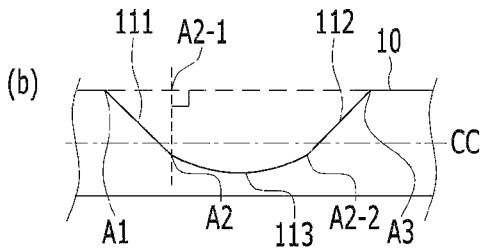
Figure 33:
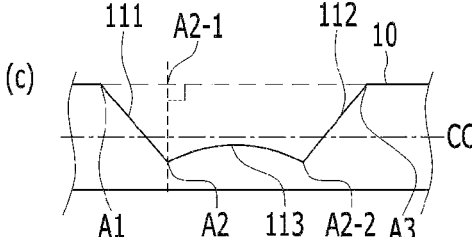

FIG. 33 is a view illustrating a cog according to an exemplary embodiment of the present disclosure. Specifically, FIG. 33 illustrates various embodiments of the intagliated cog 110 of FIG. 26.

Referring to FIGS. 33A to 33C, the cross-section of the intagliated cog 110 may be formed in the shape of a polygon with N sides (where N is a natural number that is greater than or equal to 4). In an example of FIG. 33A, the intagliated cog 110 may have a lower side 113 formed to have a straight line shape, and even in this case, the first side 111 and the second side 112 may be formed leftward and rightward from the lower side 113, the angle θ1 formed between the second side 112 and the horizontal plane of the lifting suture 10 (see FIG. 26) may be an obtuse angle, and the first-fourth point A2-1 may be positioned between the first-first point A1 and the first-third point A3.

In an example of FIG. 33B, the intagliated cog 110 may have a lower side 113 formed to have a convex shape, and even in this case, the first side 111 and the second side 112 may be formed leftward and rightward from the lower side 113, the angle θ1 formed between the second side 112 and the horizontal plane of the lifting suture 10 (see FIG. 26) may be an obtuse angle, and the first-fourth point A2-1 may be positioned between the first-first point A1 and the first-third point A3.

In an example of FIG. 33C, the intagliated cog 110 may have a lower side 113 formed to have a concave shape, and even in this case, the first side 111 and the second side 112 may be formed leftward and rightward from the lower side 113, the angle θ1 formed between the second side 112 and the horizontal plane of the lifting suture 10 (see FIG. 26) may be an obtuse angle, and the first-fourth point A2-1 may be positioned between the first-first point A1 and the first-third point A3.

Figure 34:
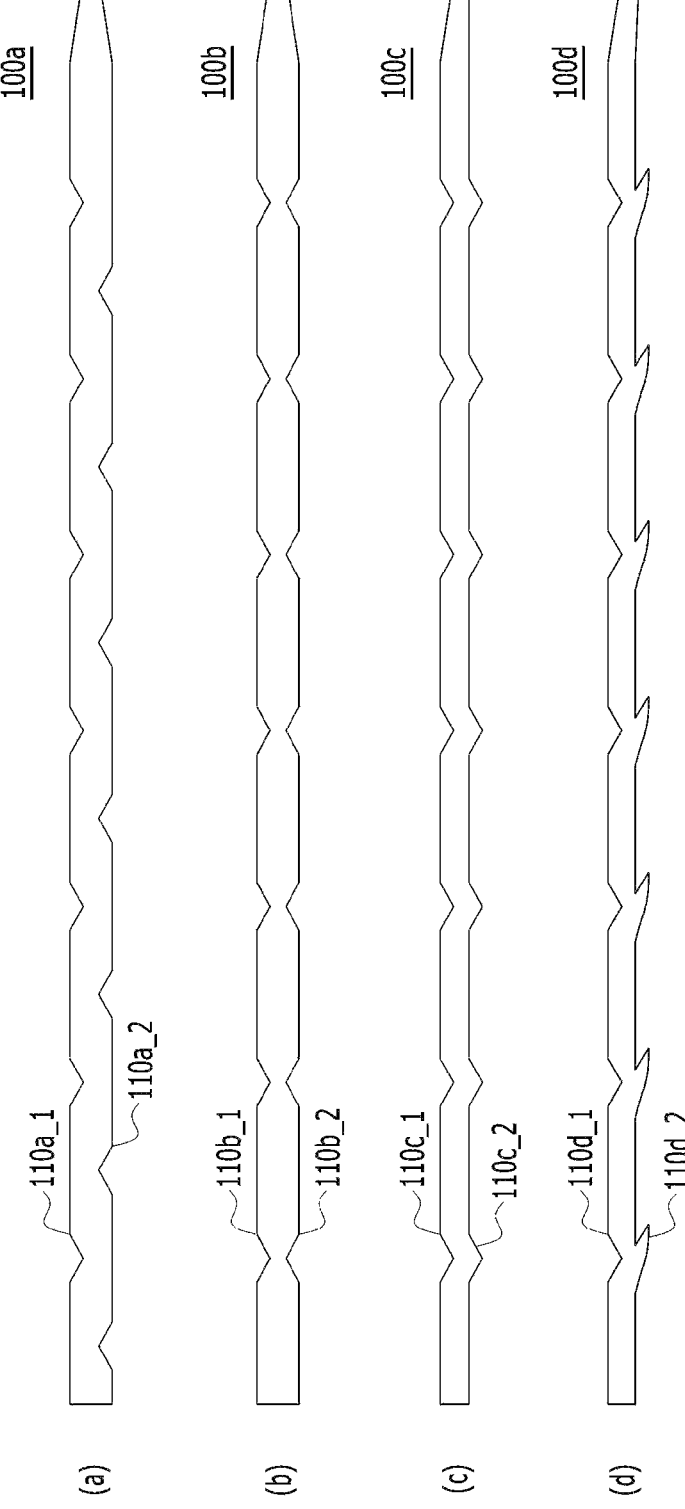
FIG. 34 is a view illustrating a first lifting portion according to an exemplary embodiment of the present disclosure.

FIG. 34 is a view illustrating a first lifting portion according to an exemplary embodiment of the present disclosure. Specifically, FIG. 34 illustrates an embodiment in which a first lifting portion includes several cogs including intagliated cogs.

Referring to FIGS. 26 and 34A, a first lifting portion 100a may include first intagliated cogs 110a_1 and second intagliated cogs 110a_2, and the first intagliated cogs 110a_1 and the second intagliated cogs 110a_2 may be disposed so that central axes thereof are alternately disposed. In the present specification, the central axis of a cog may be an axis in the width direction dw (see FIG. 26) from a vertex of the cog (for example, A2 of FIG. 26), and in an example of FIG. 34A, the first intagliated cogs 110a_1 disposed on one surface of the first lifting portion 100a and the second intagliated cogs 110a_2 disposed on the other surface of the first lifting portion 100a may be disposed so that central axes thereof are alternately disposed. According to the present embodiment, by the central axes of the intagliated cogs being alternately disposed, breakage of the lifting suture 10 may be prevented.

Referring to FIGS. 26 and 34B, a first lifting portion 100b may include first intagliated cogs 110b_1 and second intagliated cogs 110b_2, and the first intagliated cogs 110b_1 and the second intagliated cogs 110b_2 may be disposed to share a central axis with each other. That is, since the first intagliated cogs 110b_1 disposed on one surface of the first lifting portion 100b and the second intagliated cogs 110b_2 disposed on the other surface of the first lifting portion 100b are disposed to share the central axis with each other, the lifting suture 10 may be easily manufactured, and during discharge from a cannula, since the intagliated cogs on both surfaces come out at once, the discharge may be facilitated.

Referring to FIGS. 26 and 34C, a first lifting portion 100c may have intagliated cogs 110c_1 disposed on one surface and first embossed cogs 110c_2 disposed on the other surface. In one embodiment, the first embossed cog 110c_2 is a cog configured in the shape of a triangle with a relatively large vertex angle and may indicate an embossed cog having a similar shape to the intagliated cog 110 described above with reference to FIG. 26. Accordingly, the first embossed cog 110c_2 also has both side surfaces formed with a gentle slope, and thus discharge of the first embossed cog 110c_2 from the cannula may be easy. According to the present embodiment, since the first lifting portion 100c includes the intagliated cogs 110c_1 and the first embossed cogs 110c_2, while the discharge of the first lifting portion 100c from the cannula is facilitated, the catching ability due to the first embossed cogs 110c_2 may be improved, and thus convenience of treatment may be improved.

Referring to FIGS. 26 and 34D, a first lifting portion 100d may have intagliated cogs 110d_1 disposed on one surface and second embossed cogs 110d_2 disposed on the other surface. In one embodiment, the second embossed cog 110d_2 is a cog configured in the shape of a triangle with a relatively small vertex angle and may have a similar shape to the embossed cog 210 described above with reference to FIG. 26. According to the present embodiment, since the first lifting portion 100d includes the intagliated cogs 110d_1 and the second embossed cogs 110d_2, while the discharge of the first lifting portion 100d from the cannula is facilitated, the catching ability due to the second embossed cogs 110d_2 may be improved, and thus convenience of treatment may be improved.

Although an example in which a single type of cog is disposed on one surface is illustrated in FIG. 34, the technical spirit of the present disclosure is not limited thereto, and an embodiment in which different types of cogs are included on one surface of the first lifting portion 100 may also be included in the technical spirit of the present disclosure. In one example, intagliated cogs and embossed cogs may be alternately disposed on one surface of the first lifting portion.

Figure 35:
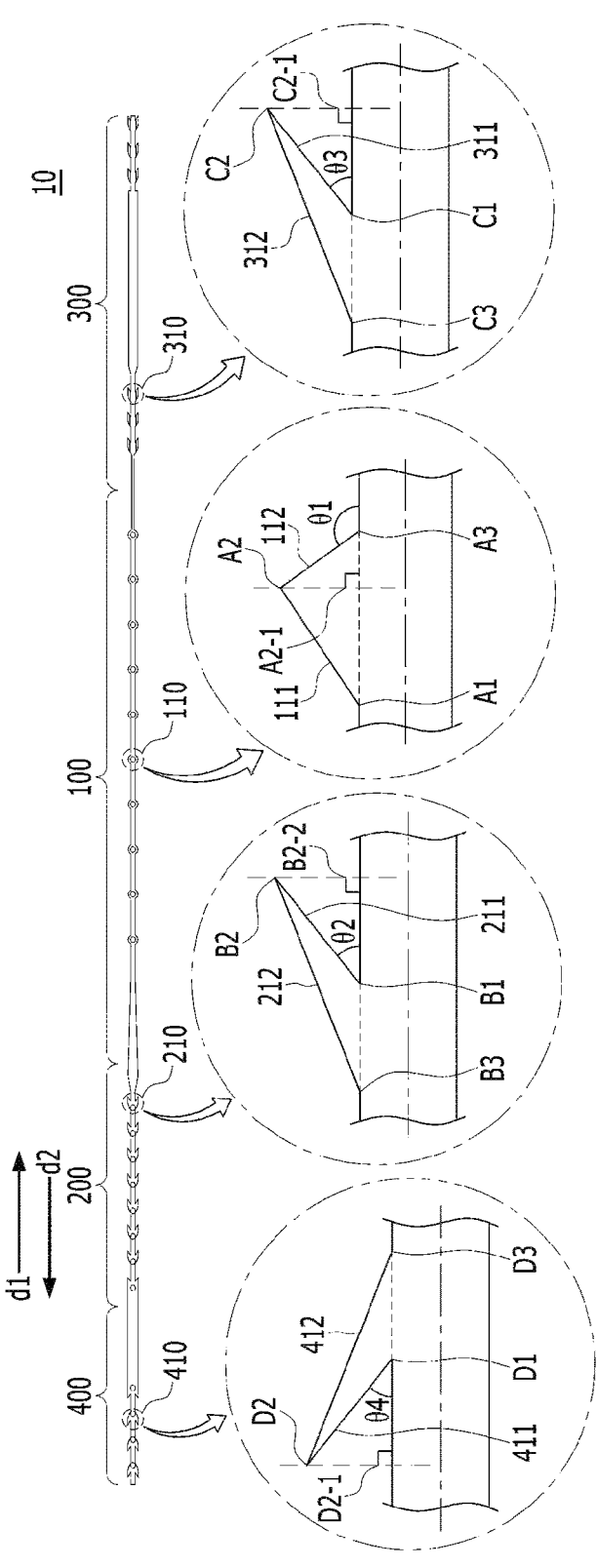
FIG. 35 is a view illustrating a lifting suture according to an exemplary embodiment of the present disclosure.

FIG. 35 is a view illustrating a lifting suture according to an exemplary embodiment of the present disclosure.

Referring to FIG. 35, the lifting suture 10 may include the first lifting portion 100 disposed at the nose bridge part of a patient, the second lifting portion 200 disposed at the columella part of the patient, a first extension 300 extending from the first lifting portion 100 in a first direction d1 and disposed at the nose bridge part of the patient, and a second extension 400 extending from the second lifting portion 200 in a second direction d2 opposite to the first direction d1 and disposed at the columella part of the patient. The lifting suture is a thread made for a surgical purpose, and in particular, a thread made for lifting treatment for lifting a nose bridge or lifting a nose tip for rhinoplasty. The lifting suture may be referred to by another name such as "lifting thread."

In one example, the lifting suture 10 may be formed by injecting and then pressing a raw material, and the raw material may include one or more of polydioxanone, polylactic acid, polyglycolic acid, polycaprolactone, and a copolymer thereof, but this is only an example, and the technical spirit of the present disclosure is not limited thereto. The lifting suture injection-molded/pressing-molded using the raw material may have an elastic property overall.

In another embodiment, the lifting suture may be made of a temperature recovery material (for example, a shape-memory alloy). In this embodiment, the lifting suture may be formed to have a predetermined angle at body temperature, an angle set to be suitable for a patient may be remembered in the lifting suture, and as the lifting suture is restored to the predetermined angle inside the body, lifting treatment may be efficiently performed.

The first lifting portion 100 may include one or more first cogs 110, the second lifting portion 200 may include one or more second cogs 210, the first extension 300 may include one or more third cogs 310, and the second extension 400 may include one or more fourth cogs 410. In the present specification, by being formed to protrude or be recessed from the lifting suture 10, the cogs may serve to be fixed to internal tissue of the nose of a patient when the lifting suture 10 is inserted into the nose of the patient and may also be referred to as protrusions. The cogs may be formed at left and right sides of the lifting suture 10 as illustrated in FIG. 35. In addition, it should be understood that cogs of certain shapes may also be formed at front and rear sides of the lifting suture 10 (a surface shown in FIG. 35 and a back surface thereof), and the cogs may be formed at any position on the circumferential surface of the lifting suture 10.

A cross-section of the first cog 110 of the first lifting portion 100 may be configured in a triangular shape with a relatively large vertex angle that has a side in contact with a surface of the lifting suture 10 as a base and a first side 111 and a second side 112 as the other two sides. The cross-section of the first cog 110 may include a first-first point A1 where the surface and the first side 111 meet and a first-third point A3 where the surface and the second side 112 meet and may further include a first-second point A2 where the first side 111 and the second side 112 meet. In one embodiment, the first cog 110 may be configured as an embossed cog with a relatively large vertex angle. In the present specification, an embossed cog may be a cog formed to protrude from the lifting suture 10, and an embossed cog with a relatively large vertex angle may be a cog configured in the shape of an acute triangle in which all angles of the triangle constituting the cog are acute. To this end, a first-fourth point A2-1 at a position where the surface of the lifting suture 10 meets a vertical line that connects the first-second point A2 of the first cog 110 to a central axis of the lifting suture 10 may be positioned between the first-first point A1 and the first-third point A3. Also, a first angle θ1 between the second side 112 of the first cog 110 and the first direction d1 may be an obtuse angle. The first side 111 may form an acute angle with the first direction d1.

A cross-section of the second cog 210 of the second lifting portion 200 may be configured in a triangular shape with a relatively small vertex angle that has a side in contact with the surface of the lifting suture 10 as a base and a third side 211 and a fourth side 212 as the other two sides. The cross-section of the second cog 210 may include a second-first point B1 where the surface and the third side 211 meet and a second-third point B3 where the surface and the fourth side 212 meet and may further include a second-second point B2 where the third side 211 and the fourth side 212 meet. In one embodiment, the second cog 210 may be configured as an embossed cog with a relatively small vertex angle. In the present specification, an embossed cog with a relatively small vertex angle may be a cog configured in the shape of an obtuse triangle in which at least one angle of the triangle constituting the cog is a right angle or an obtuse angle. To this end, a second-fourth point B2-1 at a position where the surface of the lifting suture 10 meets a vertical line that connects the second-second point B2 of the second cog 210 to the central axis of the lifting suture 10 may be positioned in the first direction d1 from the second-first point B1 and the second-third point B3. Also, a second angle θ2 between the third side 211 of the second cog 210 and the first direction d1 may be an acute angle, and the fourth side 212 may also form an acute angle with the first direction d1.

A cross-section of the third cog 310 of the first extension 300 may be configured in a triangular shape with a relatively small vertex angle that has a side in contact with the surface of the lifting suture 10 as a base and a fifth side 311 and a sixth side 312 as the other two sides. The cross-section of the third cog 310 may include a third-first point C1 where the surface and the fifth side 311 meet and a third-third point C3 where the surface and the sixth side 312 meet and may further include a third-second point C2 where the fifth side 311 and the sixth side 312 meet. In one embodiment, the third cog 310 may be configured as an embossed cog with a relatively small vertex angle that forms an acute angle with the first direction d1. To this end, a third-fourth point C2-1 at a position where the surface of the lifting suture 10 meets a vertical line that connects the third-second point C2 of the third cog 310 to the central axis of the lifting suture 10 may be positioned in the first direction d1 from the third-first point C1 and the third-third point C3. Also, a third angle θ3 between the fifth side 311 of the third cog 310 and the first direction d1 may be an acute angle, and the sixth side 312 may also form an acute angle with the first direction d1.

A cross-section of the fourth cog 410 of the second extension 400 may be configured in a triangular shape with a relatively small vertex angle that has a side in contact with the surface of the lifting suture 10 as a base and a seventh side 411 and an eighth side 412 as the other two sides. The cross-section of the fourth cog 410 may include a fourth-first point D1 where the surface and the seventh side 411 meet and a fourth-third point D3 where the surface and the eighth side 412 meet and may further include a fourth-second point D2 where the seventh side 411 and the eighth side 412 meet. In one embodiment, the fourth cog 410 may be configured as an embossed cog with a relatively small vertex angle that forms an acute angle with the second direction d2. To this end, a fourth-fourth point D2-1 at a position where the surface of the lifting suture 10 meets a vertical line that connects the fourth-second point D2 of the fourth cog 410 to the central axis of the lifting suture 10 may be positioned in the second direction d2 from the fourth-first point DI and the fourth-third point D3. Also, a fourth angle θ4 between the seventh side 411 of the fourth cog 410 and the second direction d2 may be an acute angle, and the eighth side 412 may also form an acute angle with the second direction d2.

In one embodiment, a length of the first lifting portion 100 may be formed in a range of 41 mm to 49 mm, a length of the second lifting portion 200 may be formed in a range of 18 mm to 22 mm, a length of the first extension 300 may be formed in a range of 26 mm to 32 mm, and a length of the second extension 400 may be formed in a range of 13 mm to 15 mm, and by employing the above lengths, the lifting suture 10 suitable for the nose bridge and columella of a patient may be formed.

The lifting suture 10 according to one embodiment of the present disclosure may further include the extensions 300 and 400 in addition to the lifting portions 100 and 200 disposed in the nose of the patient, and due to the extensions being additionally disposed in the nose of the patient, the volume of the lifting suture 10 disposed in the nose of the patient may increase as a result of the lifting treatment, and accordingly, the patient's satisfaction with the treatment may increase.

Also, since the first extension 300 according to one embodiment of the present disclosure includes an embossed cog with a relatively small vertex angle that forms an acute angle with the first direction d1, a fixing force to tissue of the nose bridge of the patient may be increased, and since the second extension 400 includes an embossed cog with a relatively small vertex angle that forms an acute angle with the second direction d2, a fixing force to tissue of the columella of the patient may be increased.

Figure 36:
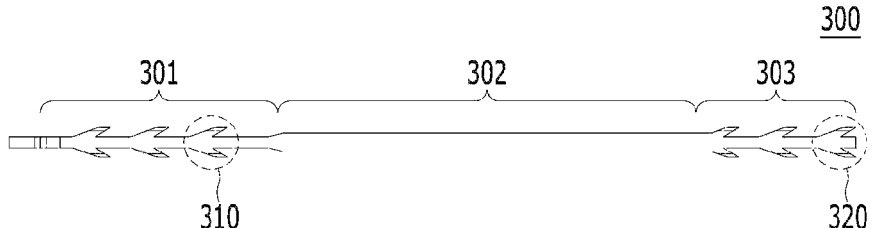
FIG. 36 is a view illustrating the lifting suture according to an exemplary embodiment of the present disclosure.

FIG. 36 is a view illustrating the lifting suture according to an exemplary embodiment of the present disclosure. FIG. 36 illustrates the first extension 300 of FIG. 35 in detail.

Referring to FIG. 36, the first extension 300 may include a first sub-extension 301. a second sub-extension 302, and a third sub-extension 303. In one embodiment, the first sub-extension 301 may include the third cog 310 having the shape of an embossed cog with a relatively small vertex angle, and the third sub-extension 303 may include a fifth cog 320 having the shape of an embossed cog with a relatively small vertex angle. In one embodiment, the second sub-extension 302 may be configured in a shape that is injection-molded/press-molded to be thick without a cog, and accordingly, additional volume may be provided to the nose bridge of the patient.

In one embodiment, the first sub-extension 301 may be formed to have a length in a range of 6 mm to 8 mm, the second sub-extension 302 may be formed to have a length in a range of 14 mm to 18 mm, and the third sub-extension 303 may be formed to have a length in a range of 6 mm to 8 mm, and accordingly, the second sub-extension 302 having a relatively large thickness may be positioned at the most suitable place for imparting volume to the nose bridge.

An example of FIG. 36 in which the first extension 300 is divided into three regions is only an embodiment, and it should be understood that the first extension 300 may be divided into two regions or four or more regions, and the regions may be configured in different shapes from each other.

Figure 37:
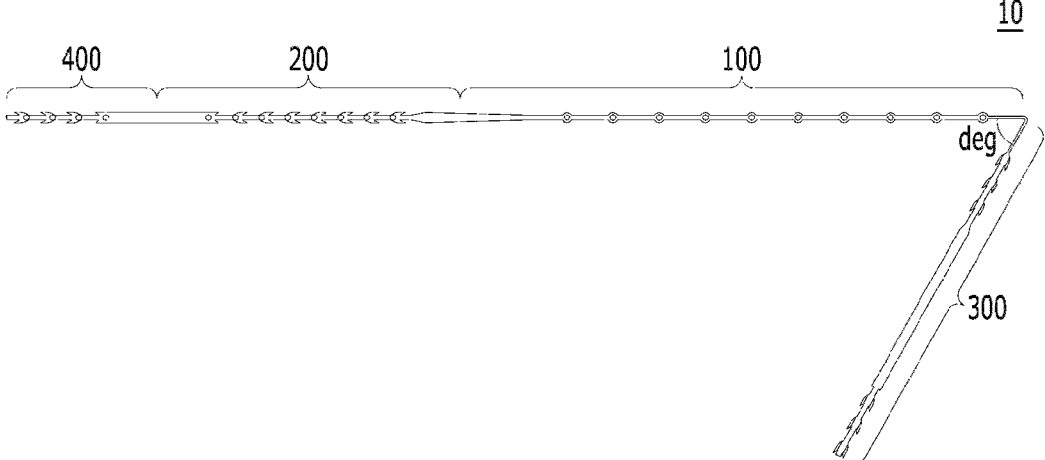
FIG. 37 is a view illustrating the lifting suture according to an exemplary embodiment of the present disclosure.

FIG. 37 is a view illustrating the lifting suture according to an exemplary embodiment of the present disclosure.

Referring to FIG. 37, the first lifting portion 100 and the first extension 300 may be formed to be bent to have a predetermined angle deg therebetween. In one embodiment, the lifting suture 10 may be formed by being pressed while the first lifting portion 100 and the first extension 300 are bent, and in another embodiment, the lifting suture 10 may be formed by being hardened after heating and bending the first lifting portion 100 and the first extension 300. In one embodiment, the first lifting portion 100 and the first extension 300 may be bent to have a predetermined radius of curvature therebetween.

In one embodiment, the predetermined angle deg may be any one angle in a range of 30° to 150°. Since the lifting suture 10 is formed while the first lifting portion 100 and the first extension 300 are bent to have the predetermined angle deg therebetween, the lifting suture 10 may be easily discharged from inside a cannula utilized in treatment and may be easily disposed in the nose bridge of a patient while the first lifting portion 100 and the first extension 300 are folded.

Although the form in which a side surface of the lifting suture 10 is bent is illustrated in FIG. 37, this is only an example, and it should be understood that the technical spirit of the present disclosure may apply regardless of a direction in which the lifting suture 10 is bent based on a portion between the first lifting portion 100 and the first extension 300.

Figure 38:
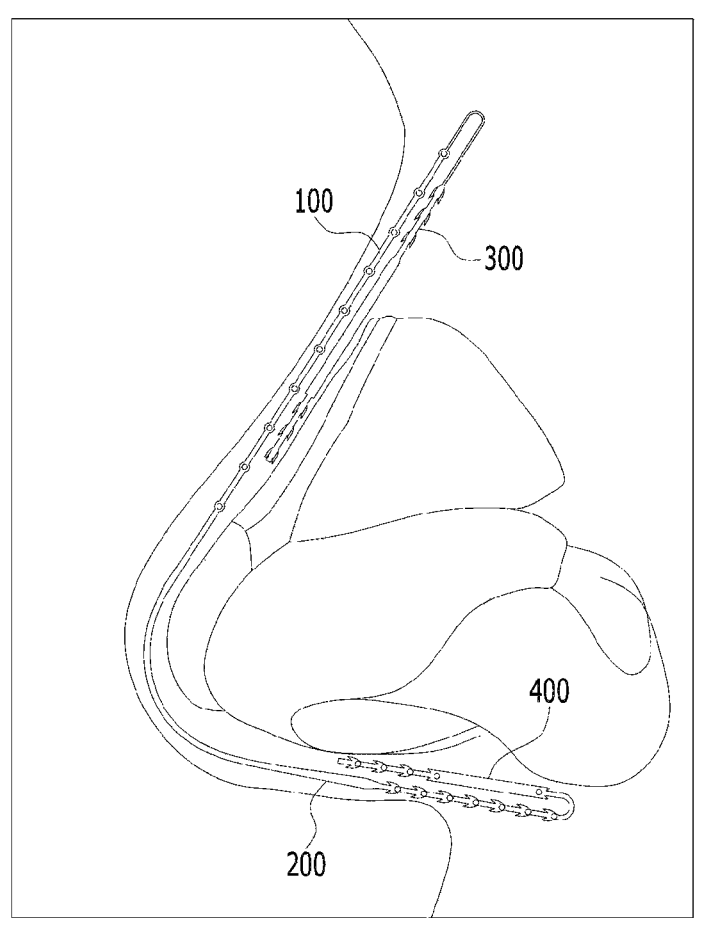
FIG. 38 is a view illustrating an embodiment in which lifting treatment is performed by utilizing the lifting suture according to an exemplary embodiment of the present disclosure.

FIG. 38 is a view illustrating an embodiment in which lifting treatment is performed by utilizing the lifting suture according to an exemplary embodiment of the present disclosure.

Referring to FIG. 38, a nose Ns of a patient may be divided into a nose bridge part P1 and a columella part P2, and through lifting treatment, the first lifting portion 100 and the first extension 300 of the lifting suture 10 may be disposed at the nose bridge part P1, and the second lifting portion 200 and the second extension 400 may be disposed at the columella part P2.

According to the technical spirit of the present disclosure, since the lifting suture 10 includes the first extension 300 and the second extension 400, space that the lifting suture 10 occupies at the nose bridge part P1 and the columella part P2 may increase compared to when the lifting suture 10 only includes the first lifting portion 100 and the second lifting portion 200, and accordingly, volume of the nose NS may increase during the lifting treatment, and the patient's satisfaction with the treatment may increase.

Also, according to the technical spirit of the present disclosure, since the first extension 300 includes a portion having a relatively thick thickness (for example, the second sub-extension 302 of FIG. 36), volume of the nose NS may be maximized, and the patient's satisfaction with the treatment may further increase.

Figure 39A:
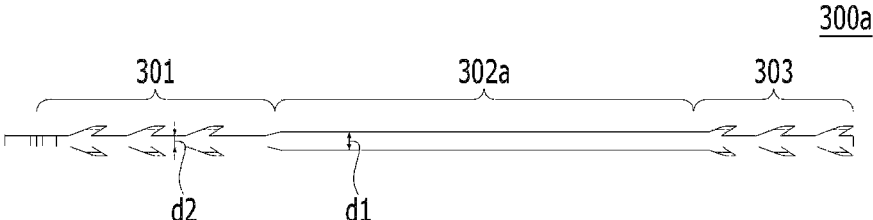
FIGS. 39A to 39C are views illustrating the lifting suture according to an exemplary embodiment of the present disclosure.
Figure 39B:
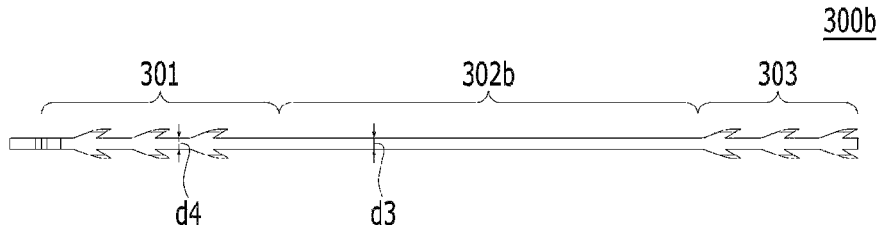
Figure 39C:
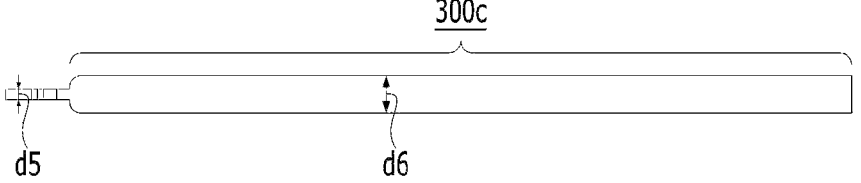

FIGS. 39A to 39C are views illustrating the lifting suture according to an exemplary embodiment of the present disclosure. Specifically, FIGS. 39A to 39C are views illustrating embodiments in which the first extension 300 employs various thicknesses.

Referring to FIG. 39A, a first extension 300a may include a first sub-extension 301. a second sub-extension 302a, and a third sub-extension 303. Also, the second sub-extension 302a may have a first thickness d1, and the first sub-extension 301 may have a second thickness d2. According to one embodiment of the present disclosure, the first thickness d1 may be formed to be thicker than the second thickness d2, and accordingly, volume of the nose may be maximized. In one example, the second thickness d2 of the first sub-extension 301 may be formed in a range of 0.6 mm to 0.7 mm, and the first thickness d1 of the second sub-extension 302a may be formed in a range of 0.8 mm to 0.9 mm, and by employing the thicknesses in the above ranges, a suitable thickness may be provided to the patient.

Referring to FIG. 39B, a first extension 300b may include a first sub-extension 301, a second sub-extension 302b, and a third sub-extension 303. Also, the second sub-extension 302b may have a third thickness d3, and the first sub-extension 301 may have a fourth thickness d4. According to one embodiment of the present disclosure, the third thickness d3 may be formed to be the same as the fourth thickness d4, and accordingly, while it is possible to form the lifting suture 10 with a relatively simple process, volume may be imparted to the nose due to employing the first extension 300b.

Referring to FIG. 39C, a first extension 300c may be formed to have a sixth thickness d6 and not include a cog. According to one embodiment of the present disclosure, the sixth thickness d6 may be formed to be thicker than a fifth thickness d5 of the first lifting portion 100, and accordingly, while it is possible to form the lifting suture 10 with a relatively simple process, volume may be imparted to the nose due to forming the first extension 300c to be thick.

Examples in which the first extension 300 employs various thicknesses are shown in FIGS. 39A to 39C, but the technical spirit of the present disclosure is not limited thereto, and of course, the technical spirit of the present disclosure may apply to various other embodiments in which volume is imparted to the nose through a change in the thickness of the first extension 300.

Figure 40A:
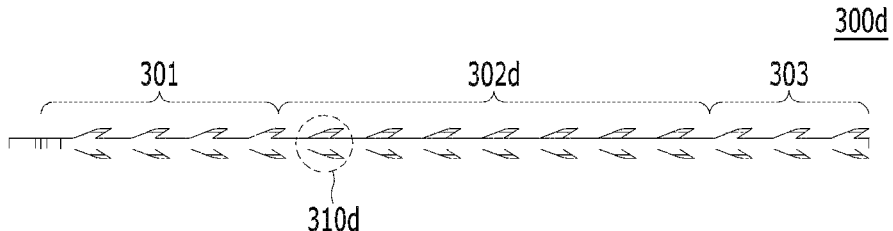
FIGS. 40A to 40C are views illustrating the lifting suture according to an exemplary embodiment of the present disclosure.
Figure 40B:
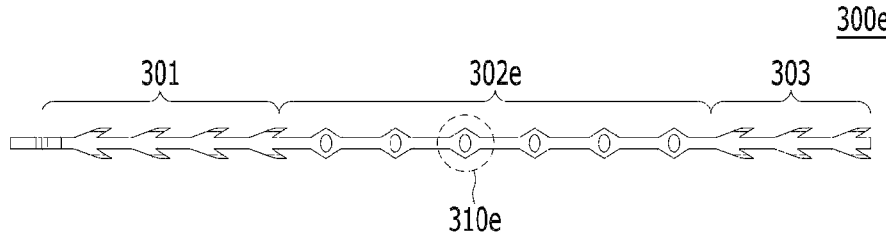
Figure 40C:
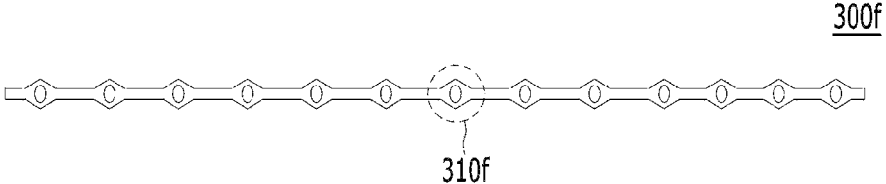

FIGS. 40A to 40C are views illustrating the lifting suture according to an exemplary embodiment of the present disclosure. Specifically, FIGS. 40A to 40C are views illustrating embodiments in which various embossed cogs are employed for the first extension 300.

Referring to FIG. 40A, a first extension 300d may include a first sub-extension 301, a second sub-extension 302d, and a third sub-extension 303. Also, the second sub-extension 302d may include an embossed cog with a relatively small vertex angle that has been described above with reference to FIG. 35 (for example, the second cog 210). According to one embodiment of the present disclosure, since embossed cogs with a relatively small vertex angle are included throughout the first extension 300d, a phenomenon in which the lifting suture is caught in tissue of the patient may be maximized, and thus a fixing force may be increased.

Referring to FIG. 40B, a first extension 300e may include a first sub-extension 301, a second sub-extension 302e, and a third sub-extension 303. Also, the second sub-extension 302e may include an embossed cog with a relatively large vertex angle that has been described above with reference to FIG. 35 (for example, the first cog 110). According to one embodiment of the present disclosure, by controlling the number of embossed cogs with a relatively large vertex angle that are included on at least a portion of the first extension 300c, the extent of the phenomenon in which the lifting suture is caught in tissue of the patient may be controlled, and a suitable fixing force may be provided to the patient.

Referring to FIG. 40C, a first extension 300f may include an embossed cog with a relatively large vertex angle that has been described above with reference to FIG. 35 (for example, the first cog 110). According to one embodiment of the present disclosure, since the entire first extension 300f is formed to include embossed cogs with a relatively large vertex angle like the first lifting portion 100, the first extension 300f may be formed by forming the first lifting portion 100 of the lifting suture 10 to extend, and accordingly, a level of difficulty of the process relating to the lifting suture 10 may be reduced, it may be easy to form the lifting suture 10 suitable for a patient by controlling the length of the first extension 300f, and the lifting suture 10 may easily come out of a cannula.

Although examples in which the first extension 300 employs various cogs are shown in FIGS. 40A to 40C, the technical spirit of the present disclosure is not limited thereto, and of course, the technical spirit of the present disclosure may apply to various other embodiments in which volume is imparted to the nose bridge by the first extension 300 employing various different kinds of cogs for each sub-extension. For example, the technical spirit of the present disclosure may also apply to an embodiment in which embossed cogs with a relatively large vertex angle are employed on the first sub-extension 301 and cogs are not included on the second sub-extension 302 and the third sub-extension 303.

Figure 41A:
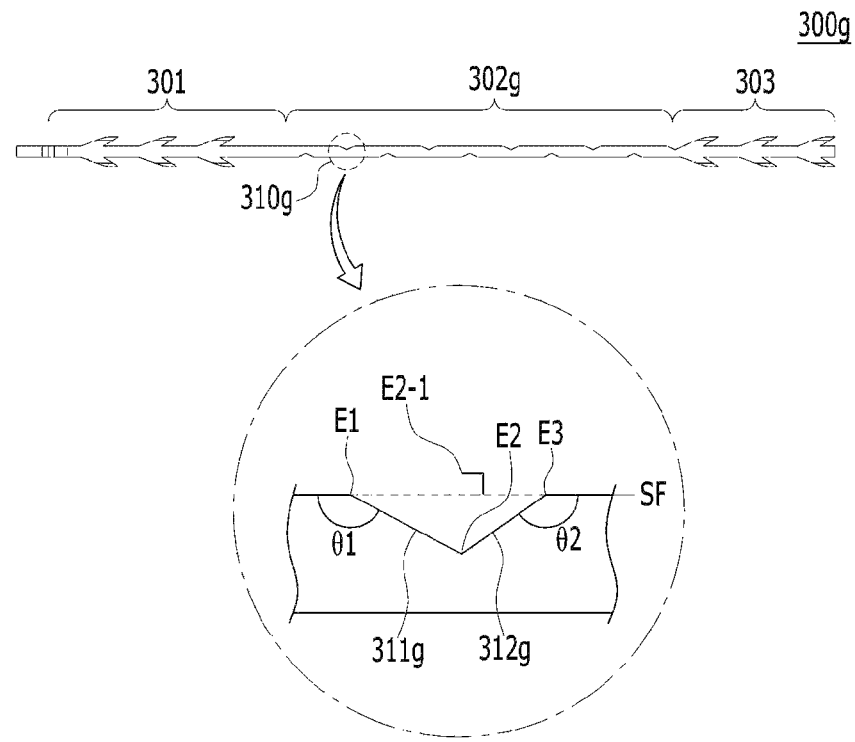
FIGS. 41A and 41B are views illustrating the lifting suture according to an exemplary embodiment of the present disclosure.
Figure 41B:
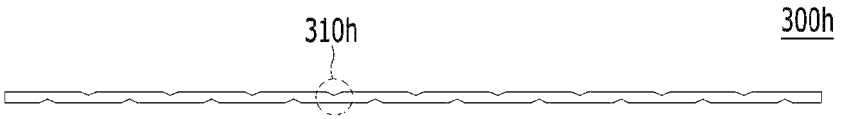

FIGS. 41A and 41B are views illustrating the lifting suture according to an exemplary embodiment of the present disclosure. Specifically, FIGS. 41A and 41B are views illustrating embodiments in which various intagliated cogs are employed for the first extension 300.

Referring to FIG. 41A, a first extension 300g may include a first sub-extension 301, a second sub-extension 302g, and a third sub-extension 303. Also, the second sub-extension 302g may include an intagliated cog 310g with a relatively large vertex angle. In the present specification, an intagliated cog may be a cog having a shape recessed inward from a surface of the lifting suture to induce a certain catching phenomenon relative to tissue of the patient, and an intagliated cog with a relatively large vertex angle may be a cog configured in the shape of an acute triangle in which all angles of the triangle formed by being intagliated are acute. To this end, a cross-section of the intagliated cog 310g with a relatively large vertex angle may include a first side 311g and a second side 312g recessed inward from a surface SF of the lifting suture 10. According to one embodiment of the present disclosure, a first angle θ1 between the first side 311g and the surface SF may be an obtuse angle or a right angle, and a second angle θ2 between the second side 312g and the surface SF may be an obtuse angle or a right angle. Accordingly, the first side 311g and the second side 312g may constitute a triangle with a relatively large vertex angle with an extension line of the surface SF, and the lifting suture 10 may be easily discharged when the cannula is discharged from the first lifting portion 100.

In the present specification, the shape of the cross-section of the intagliated cog 310g with a relatively large vertex angle may be a shape of space formed due to being recessed inward from the surface SF of the lifting suture 10 (for example, a triangular shape formed by a first-first point E1, a first-second point E2, and a first-third point E3). The cross-section of the intagliated cog 310g with a relatively large vertex angle may include the first-first point El where the surface SF and the first side 311g meet and the first-third point E3 where the surface SF and the second side 312g meet and may further include the first-second point E2 where the first side 311g and the second side 312g meet.

The intagliated cog 310g with a relatively large vertex angle according to one embodiment of the present disclosure may have a gentle slope both from one side to the other side (the first direction d1 in the example of FIG. 35) and from the other side to the one side (the second direction d2 in the example of FIG. 35). According to the technical spirit of the present disclosure, by the intagliated cog 310g with a relatively large vertex angle having the shape of a triangle with a relatively large vertex angle that has a gentle slope in both directions, the first extension 300g employing the same shape may also be easily discharged even when the lifting suture is discharged from a cannula in a reverse direction.

Referring to FIG. 41B, a first extension 300h may be formed to only include an intagliated cog 310h with a relatively large vertex angle. Accordingly, the case of discharging the first extension 300h from the cannula may be maximized, and the level of difficulty of the process may also be reduced.

Figure 42A:
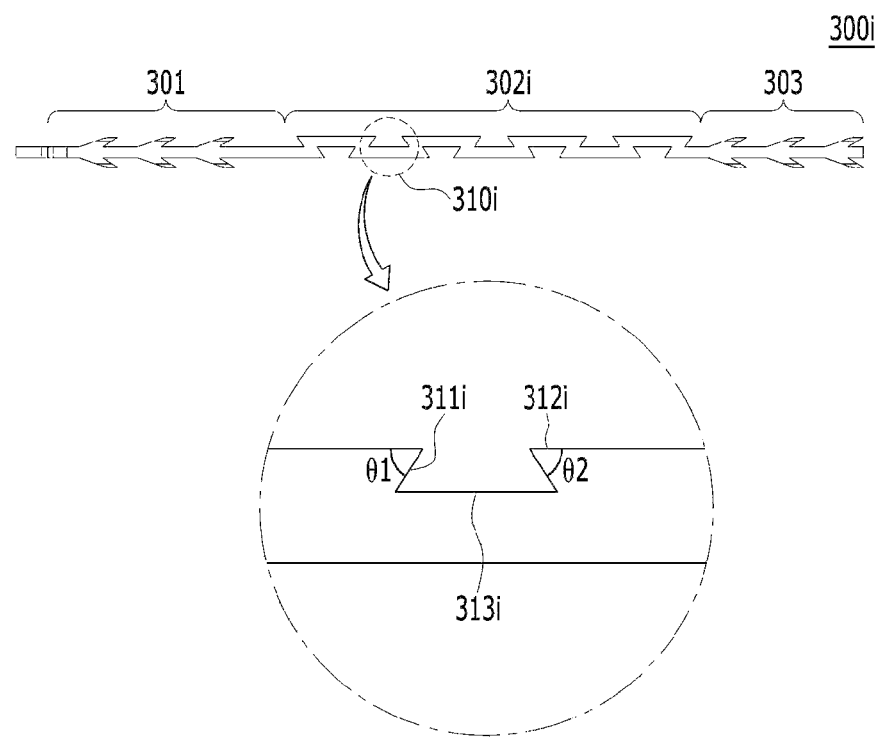
FIGS. 42A and 42B are views illustrating the lifting suture according to an exemplary embodiment of the present disclosure.
Figure 42B:
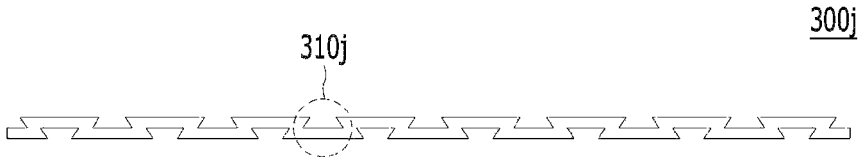

FIGS. 42A and 42B are views illustrating the lifting suture according to an exemplary embodiment of the present disclosure. Specifically, FIGS. 42A and 42B are views illustrating embodiments in which various intagliated cogs are employed for the first extension 300.

Referring to FIG. 42A, a first extension 300i may include a first sub-extension 301, a second sub-extension 302i, and a third sub-extension 303. Also, the second sub-extension 302i may include a pointed intagliated cog 310i. In the present specification, a pointed intagliated cog may be a cog configured in the shape of a rhombus in which a quadrangle formed by being intagliated has a narrow top.

To this end, a cross-section of the pointed intagliated cog 310*i* may include a first side 311*i* and a second side 312*i* recessed inward from a surface of the lifting suture 10 and a third side 313*i* between the first side 311*i* and the second side 312*i*. According to one embodiment of the present disclosure, a first angle θ1 between the first side 311*i* and the surface may be an acute angle, and a second angle θ2 between the second side 312*i* and the surface may be an acute angle. Accordingly, the first side 311*i,* the second side 312*i,* and the third side 313*i* may constitute a rhombic shape with a narrow top with an extension line of the surface, and since points where the first side 311*i* and the second side 312*i* meet the surface are formed to be pointed, a phenomenon in which the first extension 300*i* is caught in tissue during treatment may be maximized.

Referring to FIG. 42B, a first extension 300*j* may be formed to only include a pointed intagliated cog 310*j*. Accordingly, a phenomenon in which the first extension 300*j* is caught in skin tissue may be maximized, and a fixing force may be strengthened.

Although examples in which pointed embossed cogs are formed on the first sub-extension 301 and the third sub-extension 303 are illustrated in FIGS. 40A to 42B, these are only examples, and cogs of various other shapes such as an embossed cog with a relatively large vertex angle, an embossed cog with a relatively small vertex angle, an intagliated cog with a relatively large vertex angle, and an intagliated cog with a relatively small vertex angle may be disposed on the first sub-extension 301 and the third sub-extension 303.

According to a lifting suture for rhinoplasty according to the present disclosure, by utilizing a cannula, rhinoplasty for a nose bridge and a nose tip may be possible with easy and convenient treatment utilizing a single lifting suture, and specifically, changing an angle of the nose bridge and the nose tip such as lifting the nose bridge or lifting the nose tip may be possible with a single lifting suture.

Also, by performing rhinoplasty by utilizing a single lifting suture, an end of the lifting suture may not be disposed at sites such as a nose tip, and thus, while enhancing an effect of rhinoplasty, a problem in which one end of the lifting suture approaches the epidermis and causes inflammation or protrudes through the epidermis may not occur even when the lifting suture is disposed in skin tissue for a long period of time, and an effect of rhinoplasty for a nose tip can be enhanced.

According to a lifting suture for rhinoplasty according to the present disclosure, by forming a thickness of a connecting region to be thick, pressure received by a cartilage disposed at a nose tip site due to the lifting suture can be reduced, pain felt by a patient due to the treatment can be reduced, and since the nose tip is supported while deformation of or damage to the cartilage at the nose tip site is prevented, an effect of rhinoplasty for the nose tip can be enhanced.

By including two different kinds of cogs, a lifting suture according to one embodiment of the present disclosure may have a structure advantageous for securing a fixing force necessary for lifting treatment while performing the lifting treatment for a columella and a nose bridge using a single lifting suture.

Also, by having at least one cog formed of two sides forming an obtuse angle relative to a central axis, a lifting suture according to one embodiment of the present disclosure can be easily discharged from a cannula without being caught even when discharged from the cannula in a reverse direction.

By further including an extension and the extension being disposed at a columella and a nose bridge, a lifting suture according to one embodiment of the present disclosure can impart an additional thickness to the columella and nose bridge and enhance an effect of the lifting treatment.

Also, by employing an extension including various cogs, a lifting suture according to one embodiment of the present disclosure can increase a fixing force of the lifting suture and thus significantly reduce the level of difficulty of the treatment.

In addition, by employing an extension having a differentiated thickness, a lifting suture according to one embodiment of the present disclosure can implement a thicker thickness of the suture disposed in a columella and a nose bridge, and thus a patient's satisfaction with the treatment can be enhanced.

Exemplary embodiments have been described above with reference to the accompanying drawings. Specific terms have been used herein to describe the embodiments, but the terms are only used for the purpose of describing the technical spirit of the present disclosure and are not intended to limit the meaning or limit the scope of the present disclosure described in the claims. Therefore, those of ordinary skill in the art should understand that various modifications and other equivalent embodiments are possible therefrom. Accordingly, the true technical protection scope of the present disclosure should be defined by the technical spirit of the appended claims.

What is claimed is:

1. A suture for rhinoplasty, the suture consisting of:
a first region consisting of a first end point, a second end point and a first straight portion, wherein the first straight portion, which extends between the first end point and the second end point, has a first thickness and a length in a range of 3.5 cm to 4.5 cm;
a second region consisting of a third end point, a fourth end point and a second straight portion, wherein the second straight portion, which extends between the third end point and the fourth end point, has a plurality of second region cogs each having an acute angle with a longitudinal axis in a first longitudinal direction, the plurality of second region cogs being continuously disposed on the second straight portion, and wherein the second straight portion has a second thickness and a length in a range of 1.5 cm to 2.5 cm;
a connecting region consisting of the second end point, the third end point and a curved portion, wherein the curved portion, which extends between the second end point and the third end point, has a varying thickness, which is thicker than the first thickness and the second thickness, and wherein, while the connecting region is pressed to be bent, a first angle is formed between the first region and the second region;
a first extension extending from the first end point in the first longitudinal direction having a plurality of first extension legion cogs each having an acute angle with a longitudinal axis in the first longitudinal direction, the plurality of first extension legion cogs being continuously disposed on the first extension while the first extension and the first region being bent so that a second angle is formed therebetween, and wherein, when the suture is inserted into a nose, the first extension becomes positioned adjacent to the first region; and a second extension extending from the fourth end point in a second longitudinal direction opposite from the first longitudinal direction and having a plurality of second extension legion cogs, each having an acute angle with a longitudinal axis in the second longitudinal direction, the plurality of second extension legion cogs being continuously disposed on the second extension, the second region and the second extension being pressed to be bent so that a third angle is formed therebetween, and wherein, when the suture is inserted into the nose, the second extension becomes positioned adjacent to the second region, wherein the connecting region is integrally formed in which a first side close to the first region becomes integrally thicker, having a first slope, and a second side close to the second region becomes integrally thicker, having a second slope, the second slope being steeper than the first slope, and wherein a cross-sectional area at the second end point is narrower than a maximum cross-sectional area of the connecting region.

2. The suture of claim 1, wherein the first angle is in a range of 60° to 150°.

3. The suture of claim 1, wherein the first region is corresponding to a nose bridge, and the second region is corresponding to a columella.

4. The suture of claim 1, wherein:

the first side of the connecting region has a thickness increasing from the first region toward the second side of the connecting region; and the second side has a thickness increasing from the first side and then decreasing toward the second region.

5. The suture of claim 4, wherein the second side has a central portion that is thicker than two side portions of the second side surrounding the central portion.

\* \* \* \* \*